(12) United States Patent
Buchanan et al.

(10) Patent No.: US 7,938,454 B2
(45) Date of Patent: May 10, 2011

(54) STERILE CONNECTOR SYSTEMS

(75) Inventors: Bradley H. Buchanan, Sonoma, CA (US); Arnold C. Bilstad, Deerfield, IL (US); T. Michael Dennehey, Arlington Heights, IL (US); David V. Bacehowski, Grayslake, IL (US)

(73) Assignee: HyClone Laboratories, Inc., Logan, UT (US)

( * ) Notice: Subject to any disclaimer, the term of this patent is extended or adjusted under 35 U.S.C. 154(b) by 832 days.

(21) Appl. No.: 11/739,433

(22) Filed: Apr. 24, 2007

(65) Prior Publication Data

US 2008/0265561 A1 Oct. 30, 2008

(51) Int. Cl.
*F16L 33/00* (2006.01)
(52) U.S. Cl. .......................... 285/239; 285/417; 604/905
(58) Field of Classification Search .............. 285/3, 417, 285/242, 239; 604/905
See application file for complete search history.

(56) References Cited

U.S. PATENT DOCUMENTS

| | | | |
|---|---|---|---|
| 3,968,195 A * | 7/1976 | Bishop | 604/410 |
| 4,004,586 A * | 1/1977 | Christensen et al. | 604/905 |
| 4,019,512 A * | 4/1977 | Tenczar | 604/905 |
| 4,022,256 A | 5/1977 | Berkman et al. | |
| 4,157,723 A * | 6/1979 | Granzow et al. | 604/244 |
| 4,187,846 A * | 2/1980 | Lolachi et al. | 604/905 |
| 4,223,675 A | 9/1980 | Williams | |
| 4,253,500 A | 3/1981 | Williams | |
| 4,265,280 A * | 5/1981 | Ammann et al. | 604/905 |
| 4,325,417 A * | 4/1982 | Boggs et al. | 604/905 |
| 4,340,097 A * | 7/1982 | Ammann et al. | 285/3 |
| 4,356,394 A * | 10/1982 | Cobean et al. | 250/347 |
| 4,368,729 A | 1/1983 | Dossin | |
| 4,412,835 A * | 11/1983 | Spencer | 604/905 |
| 4,418,945 A * | 12/1983 | Kellogg | 604/905 |
| 4,434,822 A * | 3/1984 | Bellamy et al. | 141/98 |
| 4,500,788 A | 2/1985 | Kulin et al. | |
| 4,516,971 A * | 5/1985 | Spencer | 604/905 |
| RE32,056 E | 12/1985 | Granzow et al. | |
| 4,611,643 A * | 9/1986 | Beebe et al. | 604/905 |
| 4,620,845 A * | 11/1986 | Popovich et al. | 604/905 |
| 4,673,400 A * | 6/1987 | Martin | 604/905 |
| 4,680,025 A * | 7/1987 | Kruger et al. | 604/6.04 |
| 4,730,435 A | 3/1988 | Riddle et al. | |
| 4,774,415 A | 9/1988 | Biegel et al. | |
| 4,786,286 A | 11/1988 | Cerny et al. | |

(Continued)

FOREIGN PATENT DOCUMENTS

WO WO 82/02528 8/1982

(Continued)

OTHER PUBLICATIONS

Bill Hartzel, *Materials of Construction for Single Use Bioprocessing Systems*, Interphex 2007, Apr. 24-26, 2007.

*Primary Examiner* — David E Bochna
(74) *Attorney, Agent, or Firm* — Workman Nydegger

(57) ABSTRACT

A system for forming a fluid connection includes a first connector and a second connector. Both connectors include a tubular body having a membrane mounted on a distal end thereof. A support member facilitates the coupling of the connectors together so that the membranes are abutted together. Radiant energy is applied to the abutted membranes so as to first sterilize the membranes and then melt the membranes so that a passage is formed therethrough.

26 Claims, 18 Drawing Sheets

U.S. PATENT DOCUMENTS

| | | | |
|---|---|---|---|
| 4,807,676 A | | 2/1989 | Cerny et al. |
| 4,828,557 A | * | 5/1989 | Persidsky .................. 285/187 |
| 4,882,496 A | | 11/1989 | Bellotti et al. |
| 5,117,875 A | * | 6/1992 | Marrucchi .................. 285/3 |
| 5,409,841 A | | 4/1995 | Chow |
| 5,472,434 A | * | 12/1995 | Lechleiter .................. 604/905 |
| 5,766,744 A | | 6/1998 | Fanselow et al. |
| 5,858,016 A | | 1/1999 | Bacehowski et al. |
| 5,932,132 A | | 8/1999 | Plemons |
| 5,935,092 A | | 8/1999 | Sun et al. |
| 6,030,578 A | | 2/2000 | McDonald |
| 6,416,489 B1 | | 7/2002 | Booth |
| 2006/0110282 A1 | | 5/2006 | Bilstad et al. |

FOREIGN PATENT DOCUMENTS

| | | |
|---|---|---|
| WO | WO 84/02321 | 6/1984 |
| WO | WO 2006/107073 | 10/2006 |

* cited by examiner

STERILE CONNECTOR SYSTEMS

CROSS-REFERENCE TO RELATED APPLICATIONS

Not applicable.

BACKGROUND OF THE INVENTION

1. The Field of the Invention

The present invention relates to methods and systems for forming fluid connections including sterile fluid connections.

2. The Relevant Technology

The biotechnology and pharmaceutical industries are increasingly moving towards the use of disposable polymeric containers and tubing in their manufacturing and processing of sterile liquid product. For example, newly developed bioreactors, which are used in growing cells or microorganisms, commonly comprise a large polymeric bag-like container that is positioned within a rigid support vessel. The cells or microorganisms are grown within the polymeric bag while polymeric tubing coupled with the container is used for adding and removing material from the container. Once a batch is completed, the polymeric bag and tubing are disposed of and a new bag with tubing is used for the next batch. The use of disposable containers and tubing eliminates or at least minimizes the need for cleaning and sterilizing equipment between batches and helps improve quality control.

Although the use of disposable container systems has simplified production and processing, there are still a number of shortcomings with such systems that need to be addressed. One significant issue is how to make sterile connections for moving fluids. That is, although container systems with associated tubing can be sealed and sterilized prior to use, such as through radiation, sterile fluid connections need to be made in the field to enable movement of materials into and out of the container. Typically, such connections are made through an aseptic connection method (i.e., quick disconnect under a laminar hood or use of KLEENPAK connectors produced by Pall Corporation), steam-in-place connection method, filter connection, or a tube weld connection method. Currently, both aseptic and sterile systems available require specifically designed components and processes/methods to ensure the efficacy of the connection.

Connector systems have been made for forming sterile fluid connections on small diameter tubing used with blood bags outside of a sterile environment. Examples of such connectors are disclosed in U.S. Pat. Nos. 4,157,723; 4,265,280; and 4,325,417. Such connector systems comprise a pair of small diameter connectors each having an opaque membrane that seals the opening to the connectors closed. To facilitate a sterile fluid connection, the connectors are coupled together with the membranes adjacently disposed. A radiant energy is then applied to the connectors which melts the membranes so as to enable fluid communication between the connectors.

Although the above connectors are useful for their intended use with small diameter tubes on blood bags, the connectors are not scaleable. That is, such connectors are not designed to be scaled for use with large diameter tubing that is traditionally used by the biotechnology and pharmaceutical industries in large scale manufacturing and processing. Furthermore, such connectors typically require the fluid to pass through single or multiple sharp right angles as the fluid passes through the coupled connectors. Where cells or microorganisms are being transported, such connectors create undesirable shear forces that can damage the cells or microorganisms.

Accordingly, what is needed in the art are connection systems for forming sterile fluid connections outside of a sterile environment and which can be used with large diameter tubing for the large scale flow of sterile fluids.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

The present invention relates to connector systems for forming a sterile connection through which a sterile liquid, powder, gas, or other material can flow. As used in Detailed Description, abstract, and appended claims herein, the term "fluid connection" means a connection through which a fluid can pass but which is not limited to "fluids." For example, in different embodiments of the present invention the inventive connector systems can form "fluid connections" through which liquids, gases, powders, other forms of solids, and/or combinations thereof are intended to pass.

The connector systems can be used in a variety of different fields for a variety of different applications. By way of example and not by limitation, the connector systems can be used in the biotechnology, pharmaceutical, medical, and chemical industries in the manufacture, processing, treating, transporting, sampling, storage, and/or dispensing of sterile products such as liquids, powders, gases or the like. Examples of sterile liquid products that can be used with the connector systems include media, buffers, reagents, cell and microorganism cultures, vaccines, chemicals, blood, blood products and other biological and non-biological fluids.

The connector systems may commonly be used to selectively couple together two fluid lines, such as flexible polymeric tubing, used in the movement of a sterile fluid. The connectors, however, can also be mounted directly on a rigid or flexible container, flexible bag, and/or other equipment used in the manufacture, processing, treating, transporting, sampling, storage, and/or dispensing of sterile products.

To avoid the requirement for cleaning or maintenance, the connector systems can be designed to be disposable. Alternatively, they can also be reusable. Select embodiments of the connector systems can be uniquely adapted for use with disposable bioreactors used in growing cells and microorganisms. An example of one such bioreactor is disclosed in U.S. patent application Ser. No. 11/385,626, filed Mar. 20, 2006 which is incorporated herein by specific reference. The connector systems can be used for forming sterile connections that enable delivery of fluids, powders, gases, or the like to a bioreactor and/or dispensing cultures from the bioreactor. Once a culture is completed and dispensed from the bioreactor, the bioreactor and connectors can be disposed of.

Although the connector systems of the present invention can be used to form a sterile connection for moving sterile materials, it is appreciated that the connector systems can also be used for making connections that are non-sterile or are sterile to a limited extent. The connector systems can also be used for moving non-sterile liquids, gases, powders, and other materials.

Figure 1:
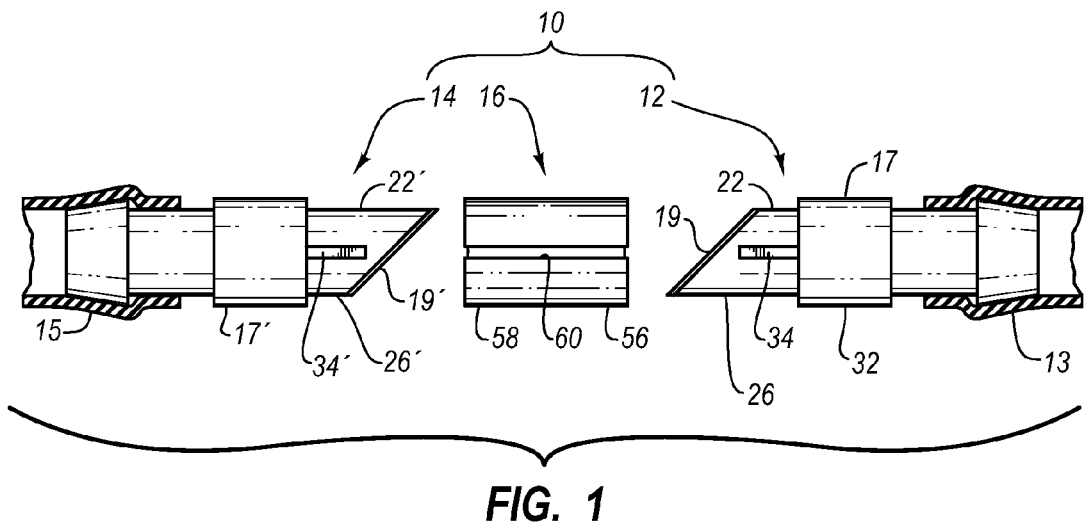
FIG. 1 is an elevated side view of one embodiment of a fluid connector system.

Depicted in FIG. 1 is one embodiment of a connector system 10 for forming a connection which incorporates features of the present invention. Connector system 10 comprises a first connector 12, a second connector 14, and a support member 16 disposed therebetween. First connector 12 is coupled with a first fluid line 13 while second connector 14 is coupled with a second fluid line 15. Fluid lines 13 and 15 can comprise flexible polymeric tubing, rigid pipe, hose, or any other form of conduit.

Figure 27:
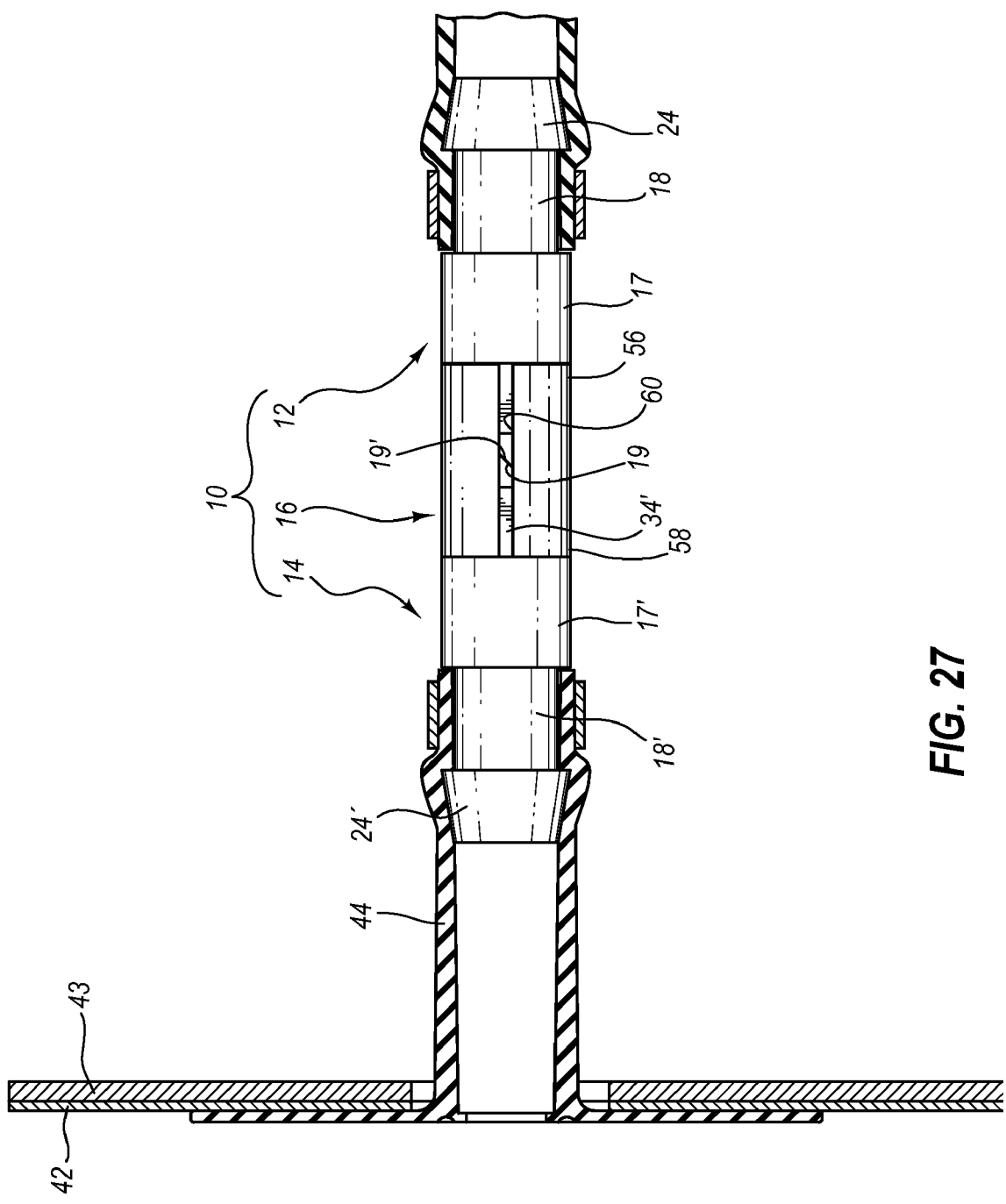
FIG. 27 is a cross sectional side view of one of the connectors shown in FIG. 1 coupled with a flexible container through a tube port.

Furthermore, as previously discussed, one or both of connectors 12, 14 need not be connected to a fluid line but can be coupled directly to a container, flexible bag, or other structure used in holding or moving fluids. For example, as depicted in FIG. 27, proximal end 24' of second connector 14 is coupled with a flexible container 42 that is disposed within a rigid support vessel 43. Connector 14 is secured to container 42 through a tube port 44 that is welded or otherwise secured to flexible container 42 and that extends out through support vessel 43. Proximal end 24' of second connector 14 is received within tube port 44 to form a sealed fluid connection therewith. Further disclosure and alternatives with regard to flexible container 42, rigid support vessel 43, and tube port 44 are disclosed in U.S. patent application Ser. No. 11/385,626 which was previously incorporated herein by specific reference.

In the depicted embodiment, first connector 12 has a configuration substantially identical to second connector 14. As such, the reference characters, elements, and disclosure with regard to first connector 12 are also applicable to second connector 14. To help maintain clarity, an apostrophe "'" is used in association with the references characters of second connector 14 where the same reference characters used to denote corresponding element of first connector 12. Making connectors 12 and 14 so that they have the same configuration simplifies the connection process and materials management or logistics.

Figure 2:
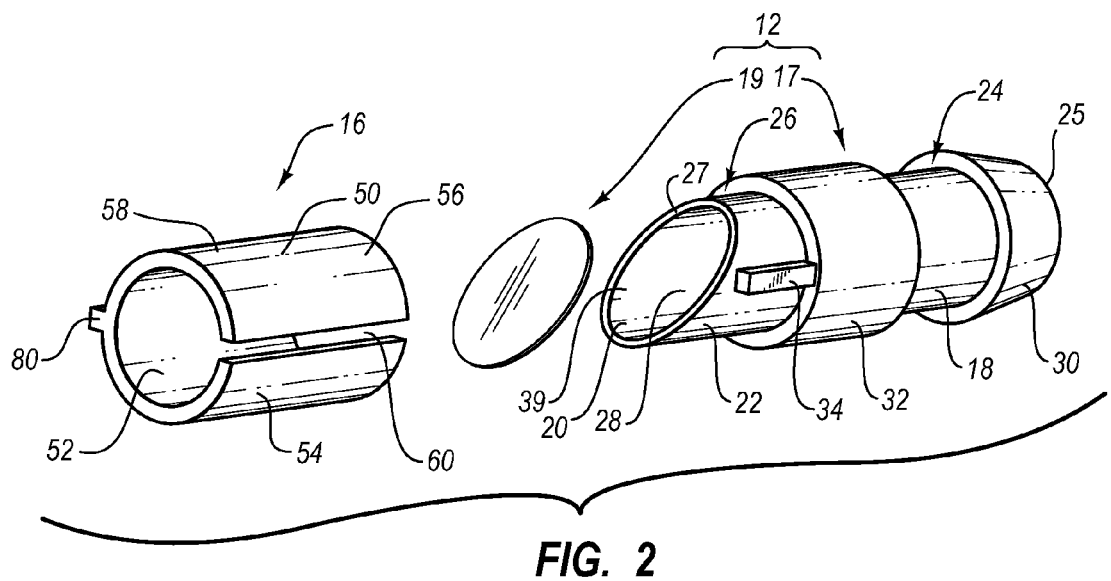
FIG. 2 is an exploded perspective view of one connector and support member of the connector system shown FIG. 1.
Figure 3:
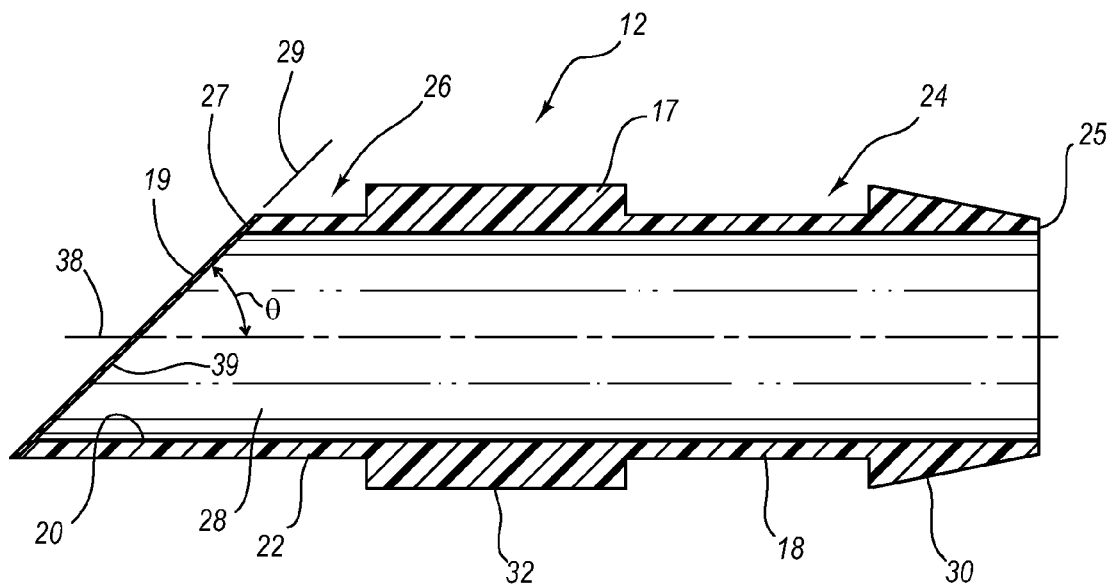
FIG. 3 is a cross sectional side view of the connector shown in FIG. 2.

As depicted in FIGS. 2 and 3, first connector 12 comprises a tubular housing 17 having a membrane 19 mounted on an end thereof. Tubular housing 17 comprises a tubular body 18 having an interior surface 20 and an opposing exterior surface 22 each extending between a proximal end 24 and an opposing distal end 26. Proximal end 24 terminates at a proximal end face 25 while distal end 26 terminates at a distal end face 27. Interior surface 20 bounds a passage 28 that extends through body 18 and has a central longitudinal axis 38 (FIG. 3). In the depicted embodiment, passage 28 is shown as being linear and extending between proximal end face 25 and distal end face 27. Passage 28 also has a transverse cross sectional area that is constant along the length of passage 28. As best shown in FIG. 3, in one embodiment distal end face 27 is disposed in an imaginary plane 29 that intersects with axis 38 so as to form an inside angle θ in a range between about 20° to about 80° with about 45° to about 70° or about 35° to about 55° being more common. Other angles can also be used, particularly with alternative designs and equipment adjustment.

One of the unique benefits of the present invention is that select embodiments of connector system 10 can be formed with a large diameter passage 28 so as to enable large flow rates therethrough. In the depicted embodiment passage 28 has a circular transverse cross section. The diameter of passage 28 can be in a range from about 1 cm to about 5 cm or about 2 cm to about 5 cm or about 3 cm to about 5 cm. Larger and smaller diameters can also be used. For example, passage 28 can also have a diameter in a range between about 0.2 cm to about 2 cm. In alternative embodiments it is appreciated that passage 28 need not have a circular transverse cross section but can be square, oval, elliptical, irregular, or have other polygonal configurations. In such other transverse cross sectional configurations, the range of transverse cross sectional surface areas can correspond to the surface areas based on the above diameters for circular passage 28. Because passage 28 has a circular transverse cross section and because distal end face 27 is angled relative axis 38, an opening 39 of passage 28 that is bounded by distal end face 27 has an elliptical configuration.

Housing 17 further comprises an annular barb 30 that encircles and radially outwardly projects from body 18 at proximal end 24. Barb 30 is merely one example of a mechanism that can be used for forming a sterile tight coupling with first fluid line 13 (FIG. 1). In alternative embodiments, it is appreciated that barb 30 can be eliminated or be replaced with an annular rib or other structure for forming a fluid tight connection first fluid line 13. Where barb 30 is eliminated, various fasteners or fastening techniques such as clamps, press fit connection, ties, welding, crimp, or the like can be used to secure body 18 to first fluid line 13 or to any other structure for which a sterile coupling is desired.

As shown in FIG. 2, a shoulder 32 encircles and radially outwardly projects from body 18 at a location between proximal end 24 and distal end 26. As will be discussed below in greater detail, shoulder 32 in part functions as a stop to help properly position support member 16 relative to connectors 12 and 14. In alternative embodiments shoulder 32 need not completely encircle body 18 but can comprise one or more shoulder sections that radially project out from body 18. In yet other embodiments shoulder 32 can be eliminated entirely. A tab 34 outwardly projects from exterior surface 22 of body 18 at a location between shoulder 32 and distal end face 27. Tab 34 interacts with support member 16, as will be discussed below in greater detail, to ensure proper alignment between connectors 12 and 14. In alternative embodiments, tab 34 can be eliminated or can be replaced with other structures that facilitate proper alignment.

In the depicted embodiment housing 17 is formed, such as by molding or cutting, so as to comprise a single, integral, unitary structure that is made from a single piece of material. In other embodiments, as will be discussed below, housing 17 can comprise two or more members that are connected together and/or can be comprised of two or more types of material.

Housing 17 is typically comprised of a transparent or semi-transparent material that allows light and/or other forms of radiant energy to pass therethrough without substantially absorbing the radiant energy. In alternative embodiments, housing 17 can be comprised of an opaque material that has one or more windows formed thereon from a transparent or semi-transparent material. Transparent materials are desirable not only because transparent materials typically have low absorption of radiant energy but also because it is desirable to be able to visually see through housing 17 to confirm the status of membrane 19 as will be discussed below. Housing 17 is also typically made of a material that is biologically and/or chemically compatible with the fluids that will pass therethrough and that does not leach or emit contaminates when exposed to fluids or to radiant energy. In addition, it is desirable that the material for housing 17 enable membrane 19 to be bound thereto and that the material can withstand conventional sterilization processes, such as radiation, without degradation or emitting unwanted contaminates. It is appreciated that housing 17 can be made of a rigid material, a flexible material, or combinations thereof.

Examples of typical materials from which housing 17 can be formed include thermoplastics. Examples of thermoplastics include acrylics such as poly(methyl methacrylate) (PMMA); polycarbonates such as those sold under the trademark LEXAN; fluoropolymers such polyvinylidene fluoride (PVDF), ethylene-tetrafluoroethylene (ETFE), and ethylene chloro-trifluoroethylene (ECTFE); and ceramics. The fluoropolymers include homopolymers and co-polymers of vinylidene fluoride of which PVDF is an example. In one embodiment various grades of PVDF are sold under the trademark KYNAR by Arkema, Inc. PVDF has desirable properties in that it is highly non-reactive and does not bind with lipids. Once specific example of KYNAR that can be used for housing 17 is KYNAR 720. Other grades and types PVDF can also be used.

Figure 4:
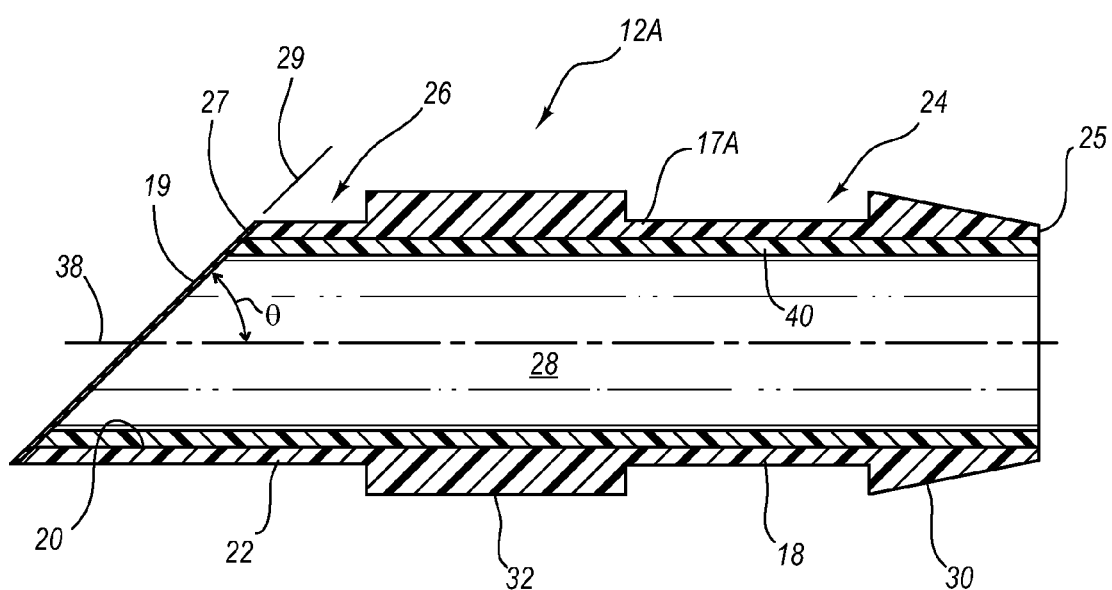
FIG. 4 is a cross sectional side view of an alternative embodiment of the connector shown in FIG. 3.

PVDF is transparent for thin sections but becomes less transparent as it gets thicker. Accordingly, in one alternative embodiment, as depicted in FIG. 4, a connector 12A comprises a housing 17A and membrane 19. Housing 17A comprises body 18, barb 30 and shoulder 32, as previously discussed, but also includes an annular contact layer 40 formed on interior surface 20 of body 18 which encircles passage 28. As such, the fluid passing through housing 17A only contacts contact layer 40. Contact layer 40 can be comprised of PVDF while the remainder of housing 17A can be comprised of an acrylic, polycarbonate, or other material. This configuration provides a transparent housing that uses the beneficial properties of PVDF. Housing 17A can be manufactured using an overmolding process or other conventional techniques.

Figure 5:
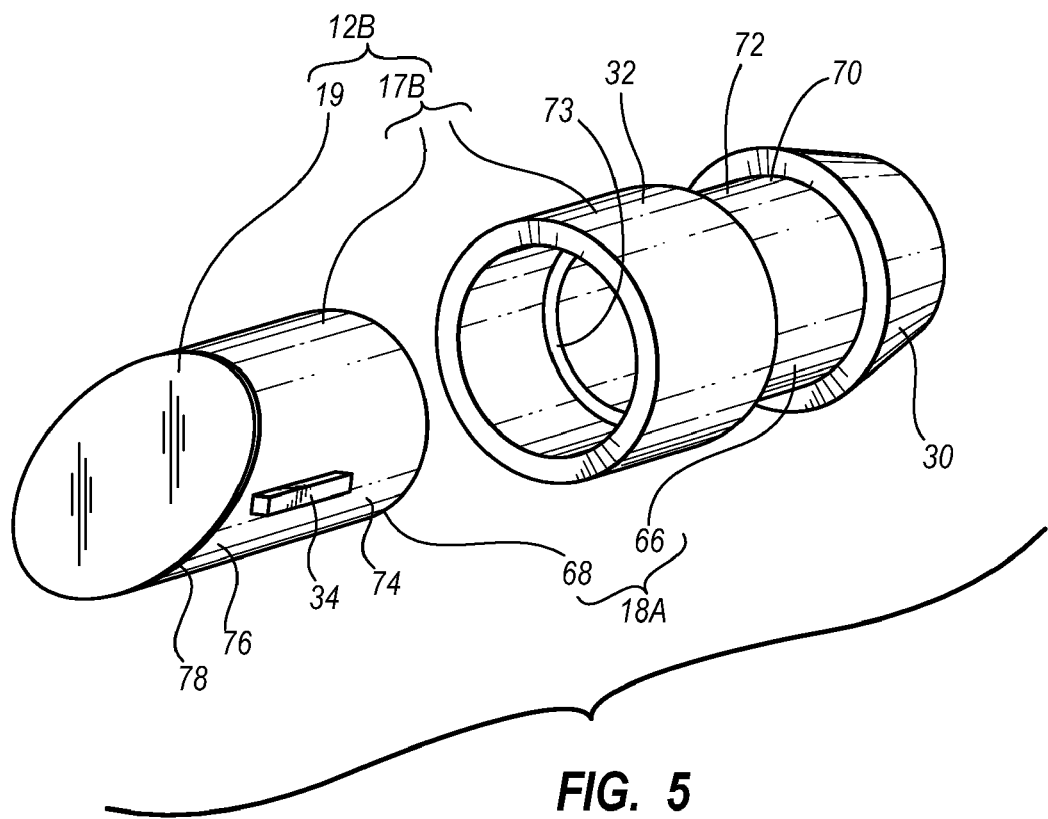
FIG. 5 is an exploded perspective view of an alternative embodiment of the connector shown in FIG. 2 wherein the connector is comprised of two separate parts.

Depicted in FIG. 5 is another alternative embodiment of a connector 12B which comprises a housing 17B and membrane 19. Housing 17B comprises a tubular body 18A which comprises a tubular first body portion 66 and a tubular second body portion 68. First body portion 66 has a proximal end 70 from which annular barb 30 radially outwardly projects and has an opposing distal end 72 from which shoulder 32 encircles and radially outwardly projects. Distal end 72 of first body portion 66 terminates at a distal end face 73 Shoulder 32 axially extends beyond distal end face 73. Second body portion 68 also has a proximal end 74 and an opposing distal end 76. Distal end 76 terminates at a distal end face 78 having a configuration and orientation the same as distal end face 27 previously discussed. Membrane 19 is mounted on distal end face 78. Proximal end 74 can be selectively received within shoulder 72 so as to butt against distal end face 73. Second body portion 68 can be coupled with shoulder 32 by using conventional techniques such as welding, clamping, adhesive, press-fit connection, or other conventional techniques.

As previously mentioned, in some embodiments it is desirable to bond membrane 19 directly to the distal end face of the housing. To accomplish this, it is typically required that the membrane be a material that is compatible with the housing. Furthermore, mounting membrane 19 over the distal opening of housing 17 can be a complex process. By forming housing 17B as a two-part member, a number of potential benefits are achieved. For example, body portions 66 and 68 can be made of different materials. By way of example, second body portion 68 can be designed to be more compatible with membrane 19 and/or have other beneficial properties while first body portion 66 can be formed from a material that is sufficiently rigid to provide secure sealed engagement with first fluid line 13. In this regard, first body portion 66 with accompanying barb 30 and sleeve 32 may be formed from a rigid material such as acrylic while second body portion 68 can be comprised of a softer more flexible material. By making second body portion 68 out of a flexible material, less stress is placed on the sealed connection between corresponding connectors 12 and 14 when they are sealed together at membranes 19 as will be discussed below in greater detail. Second body portion 68 can also be made out of the same material as membrane 19 such as PVDF.

In still other embodiments, first body portion 66 with or without accompanying sleeve 32 can be made of a flexible material. In this embodiment barb 30 can be eliminated and first body portion 66 can be configured to receive an annular barb therein such as when mounted on the end of fluid line 13 or a related connector.

Forming second body portion 68 separate from first body portion 66 can have added benefits in how membrane 19 is connected to second body portion 68. For example, where first body portion 66 with sleeve 32 and barb 30 must be molded or cut, second body portion 68 can potentially be extruded due to its simple shape. Membrane 19 can potentially be attached thereto as part of or in series with the extrusion process.

It is appreciated that housings 17, 17A and 17B can be comprised of a variety of other polymeric materials or combinations thereof, especially where limited leaching can be tolerated. In contrast to using polymeric materials, it is also appreciated that other materials such as glass, fiberglass, and composites can also be used.

As will be discussed below in greater detail, membranes 19 serve a variety of different functions. For example, prior to coupling together connectors 12 and 14, membranes 19 function to seal the distal end of each connector 12, 14 so that passages 28 remain sterile. During operation, membranes 19 of connectors 12, 14 are butted against each other. Radiant energy is then applied to abutted membranes 19 so that they melt together and form a sterile connection therebetween. As part of forming the serial connection, membranes 19 need to initially heat to a sufficient temperature, prior to melting, to destroy any unwanted contaminate or organism that may be disposed on the exposed surface of membranes 19.

Once membranes 19 have been sterilized by the heat, it is desirable that membranes 19 rapidly melt so as to avoid undo delays in forming the sterile connection. As membranes 19 melt, it is desirable that spores, organisms, or other contaminates disposed on membranes 19 be encapsulated into the melting membranes. Likewise, during the heating and melting processes and also during contact with the fluid, it is desired that the membranes not leech contaminates or emit volatiles. It is also desirable that the membranes 19 can withstand conventional sterilization processes, such as gamma radiation, without degradation, melting, or emitting unwanted contaminates. Finally, it is beneficial if membranes 19 can melt together so as to not only form a seal between connectors 12 and 14 but also form a strong structural connection between connectors 12 and 14.

In one embodiment membrane 19 is comprised of a polymer matrix having a pigment disposed therein. The polymer matrix can comprise fluoropolymers including homopolymers and co-polymers of vinylidene fluoride. One example of a homopolymer of vinylidene fluoride that can be used is polyvinylidene fluoride (PVDF) as previously discussed. One grade of PVDF that can be used is KYNAR 710, although other grades and types of PVDF can also be used. Other thermoplastics such as polypropylene and polyethylene can also be used. Such other polymers, however, may not have all of the benefits of using PVDF.

Pigmentation is added to make membrane 19 opaque and absorbent to radiant energy. By way of example and not by limitation, the pigmentation typically comprises powdered charcoal, activated charcoal, carbon black, channel black or other pigments that are absorbent of radiant energy. The pigment is added to the polymeric matrix so that the membrane has an optical density sufficient to absorb radiant energy to melt the membrane. Specifically, if the optical density is too low, too much of the radiant energy passes through the membrane without being absorbed. As a result, either the membrane does not absorb sufficient radiant energy to melt or the melting occurs over an unreasonably long time period. Alternatively, if the optical density is too high, all of the radiant energy can be absorbed on just the exterior surface of the membrane as opposed to being absorbed across the entire thickness of the membrane. This configuration can also slow or prevent optimal melting of the membrane. Thus, in some embodiments it is desirable that the optical density be such that the radiant energy can pass through the membrane so that the membrane is heated across its entire thickness but that all or at least a substantial portion of the radiant energy is absorbed by the membrane.

By way of example and not by limitation, in one embodiment carbon black or some other pigment is added to the polymeric matrix in an amount of at least about 1.5% by weight or commonly at least about 2% by weight. Other percentages can also be used. As a result of the pigment, membrane 19 has an optical density in a range between about 80 and about 99 with a range between about 90 and about 99 being more common. Other optical densities can also be used. Membrane 19 typically has a thickness in a range between about 0.0025 mm to about 0.25 mm with about 0.025 mm to about 0.125 mm being more common and about 0.05 mm to about 0.07 mm being still more common.

As previously discussed with regard to FIG. 2, membrane 19 is mounted on distal end face 27 of housing 17 so as to seal passage 28 closed. Membrane 19 is shown having an elliptical configuration that corresponds to the elliptical configuration of distal end face 27. In alternative embodiments, however, membrane 19 can have any of the alternative configurations as previously discussed with regard to passage 28, including, but not limited to circular, polygonal, or irregular. The size of membrane 19 will also depend on the size of passage 28. Depending on intended use, membrane 19 can have a maximum diameter in a range from about 1 cm to about 5 cm or about 2 cm to about 5 cm or about 3 cm to about 5 cm. Larger and smaller maximum diameters can also be used. For example, membrane 19 can also have a maximum diameter in a range between about 0.2 cm to about 2 cm.

Membrane 19 can be mounted on distal end face 27 of housing 17 using a variety of different techniques such as heat welding, sonic welding, vibrational welding, adhesive, or through any number of different mechanical connection techniques such as a clamp, compression ring, crimp, or the like.

Figure 6:
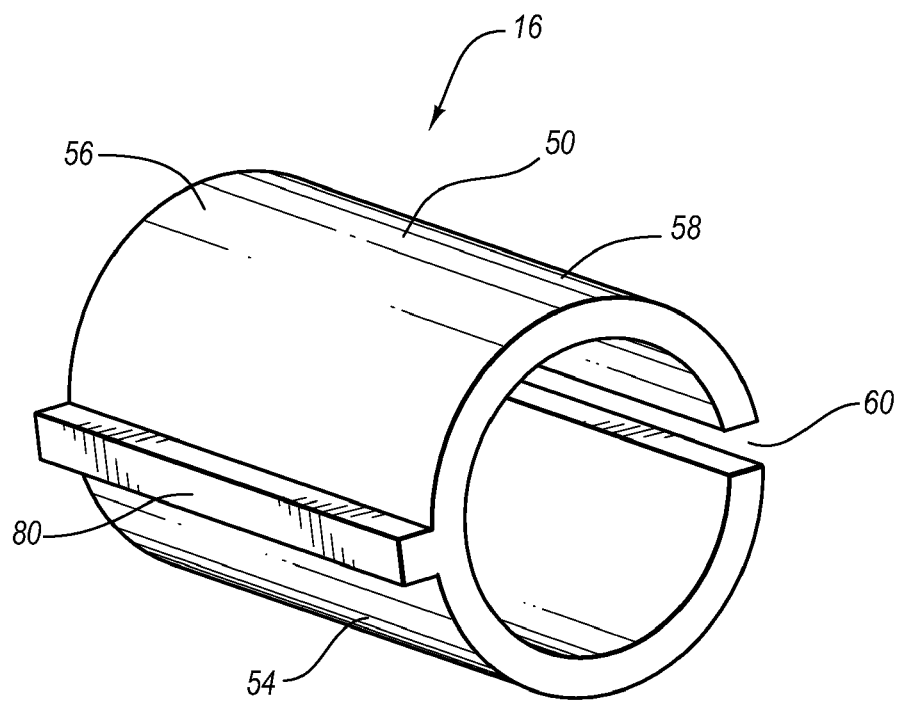
FIG. 6 is a perspective back view of the support member shown in FIG. 2.

Continuing with FIG. 2, support member 16 comprises a tubular sleeve 50 having an interior surface 52 and an exterior surface 54 extending between a first end 56 and an opposing second end 58. A linear slot 60 extends through sleeve 50 between opposing ends 56 and 58 so that sleeve 50 has a substantially C-shaped configuration when viewed from either end. Slot 60 has a width substantially equal to the width of tab 34 so that tab 34 can be slidably received within slot 60. Interior surface 52 of sleeve 50 has a configuration complementary to the exterior surface 22 of body 18 so that body 18 can be selectively and snugly received within sleeve 50. As depicted in FIGS. 2 and 6, an elongated alignment key 80 outwardly projects from exterior surface 54 of sleeve 50 and extends along the length of sleeve 50. Although not required, in the depicted embodiment alignment key 80 is disposed opposite of slot 60. In alternative embodiments, sleeve 50 can be comprised of a tube or continuous annular sleeve, two separate halves of a tube that are selectively connected together, or other support structure such as a clamp, latch or other superstructure.

Support member 16 is typically comprised of a transparent or semi-transparent material that allows light and/or other forms of radiant energy to pass therethrough without substantially absorbing the radiant energy. Although not required, support member 16 can be made of the same materials as previously discussed with regard to housing 17. Support member 16 can also be made from an opaque material having one or more openings or transparent windows formed thereon.

Prior to coupling together connectors 12 and 14, proximal ends 24 of connectors 12, 14 are coupled to a corresponding structure, such as fluid lines 13 and 15, that are either previously sealed or subsequently sealed. The structures can also include flexible bags, containers, or other type reservoirs that are directly coupled to the connectors or are coupled to fluid lines 13 and 15. After assembly, connectors 12 and 14 with their corresponding sealed structures are sterilized such as through radiation so that the compartments bounded therein are sterile. The sterile assemblies can then be shipped to their intended field use.

Figure 7:
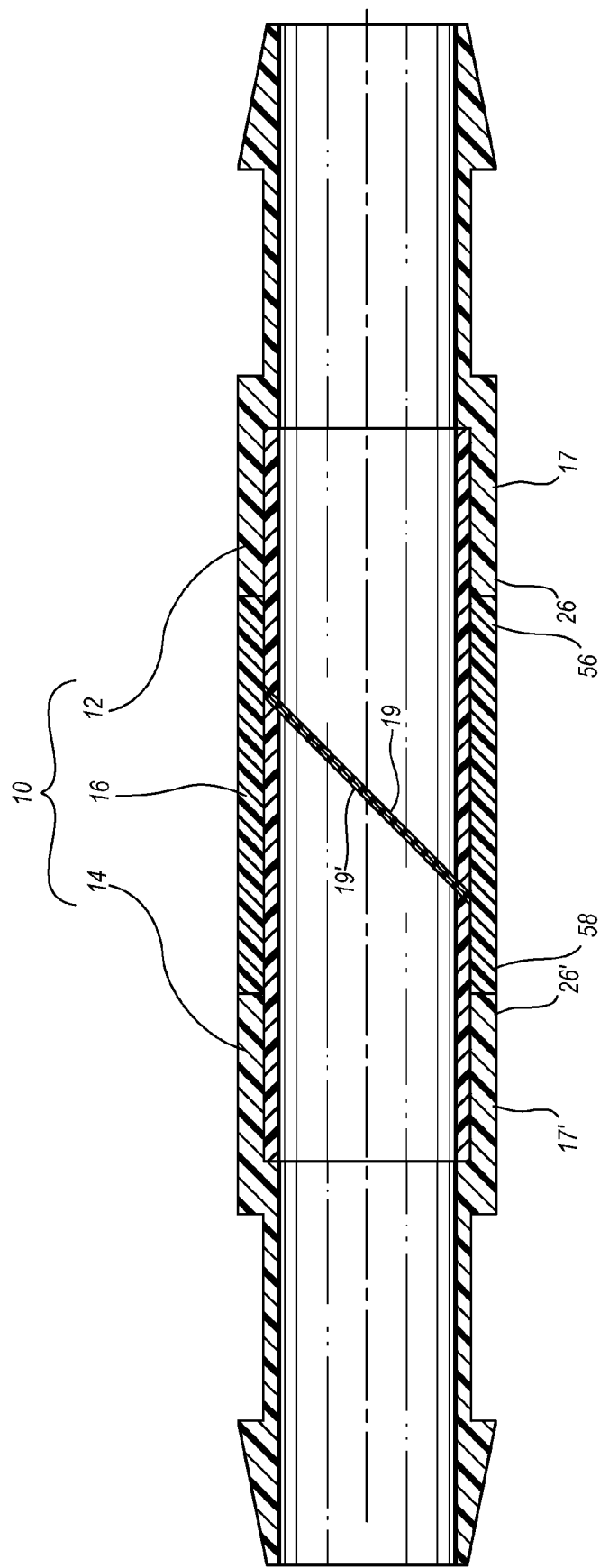
FIG. 7 is a cross section side view of the assembled connector system shown in FIG. 1.

When it is desired to make a sterile fluid connection between connectors 12 and 14, distal end 26 of first connector 12 is slid into first end 56 of support member 16. Tab 34 is aligned with and slides within slot 60 to ensure proper alignment of connectors 12 and 14. First connector 12 is advanced until support member 16 biases against shoulder 32. Next, distal end 26' of connector 14 is advanced into second end 58 of support member 16 with tab 34' being positioned within slot 60. Second connector 14 is advanced until membrane 19' of second connector 14 biases against membrane 19 of first connector 12 within support member 16 as depicted in FIG. 7. In this configuration, support member 16 not only acts as a guide to ensure proper alignment and positioning of membranes 19 and 19' but also provides structural support for the subsequent connection between connectors 12 and 14.

In one embodiment it is appreciated that an axial force can be applied to first connector 12 and second connector 14 so as to press and hold membranes 19 and 19' together. This axial force can be maintained through the melting of membranes 19 and 19' as discussed below. The axial force can be applied through various clamps, latches, fasteners and the like extending between connectors 12 and 14. Support member 16 can also be configured with locking features, such as threads or teeth, that engage with connectors 12 and 14. The locking features would enable membranes 19 and 19' to be manually biased together as connectors 12 and 14 are coupled to support member 16 and then retain that biasing force.

Figure 8:
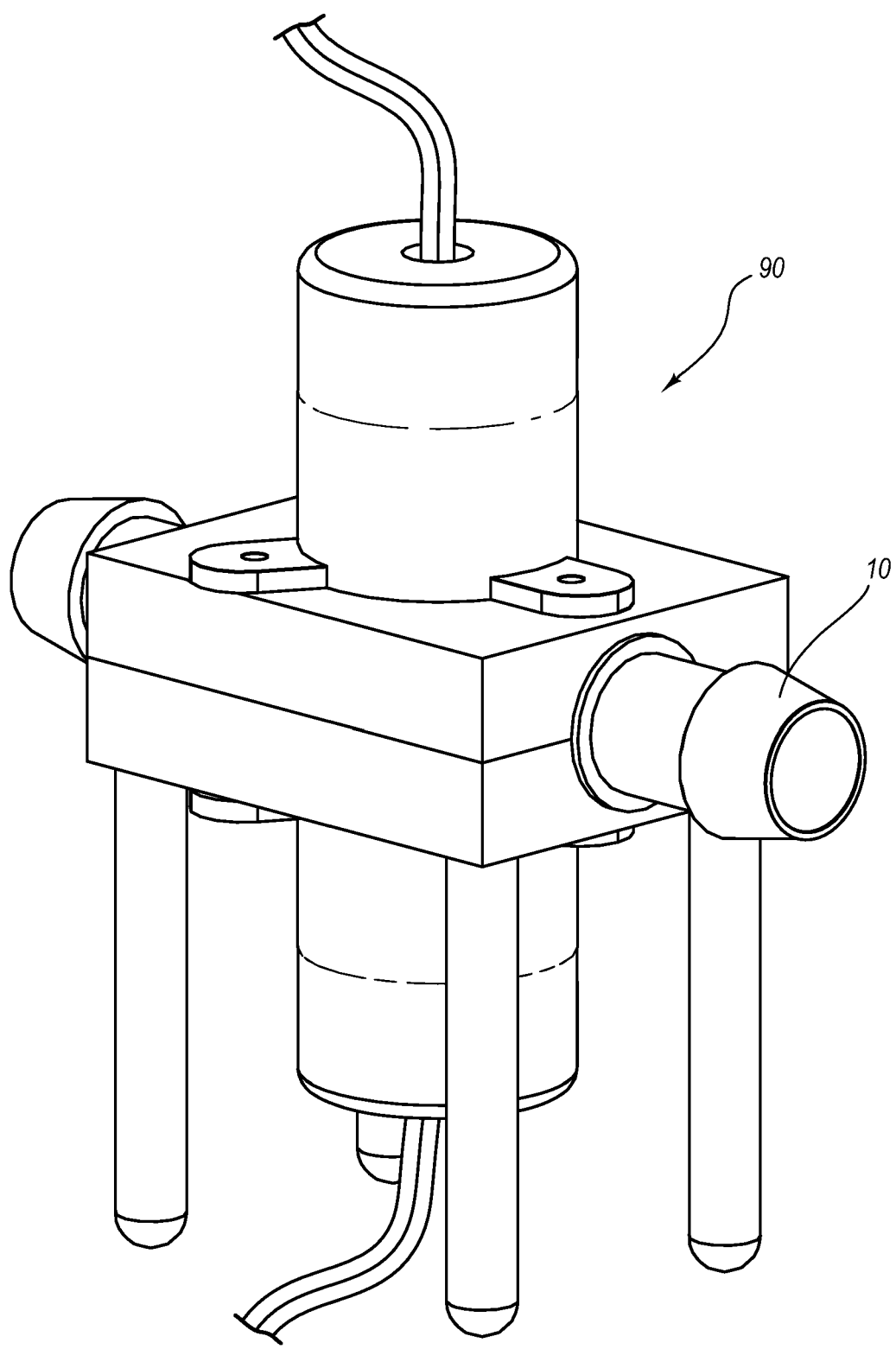
FIG. 8 is a perspective view of the connector system shown in FIG. 10 being mounted on a lamp system.
Figure 9:
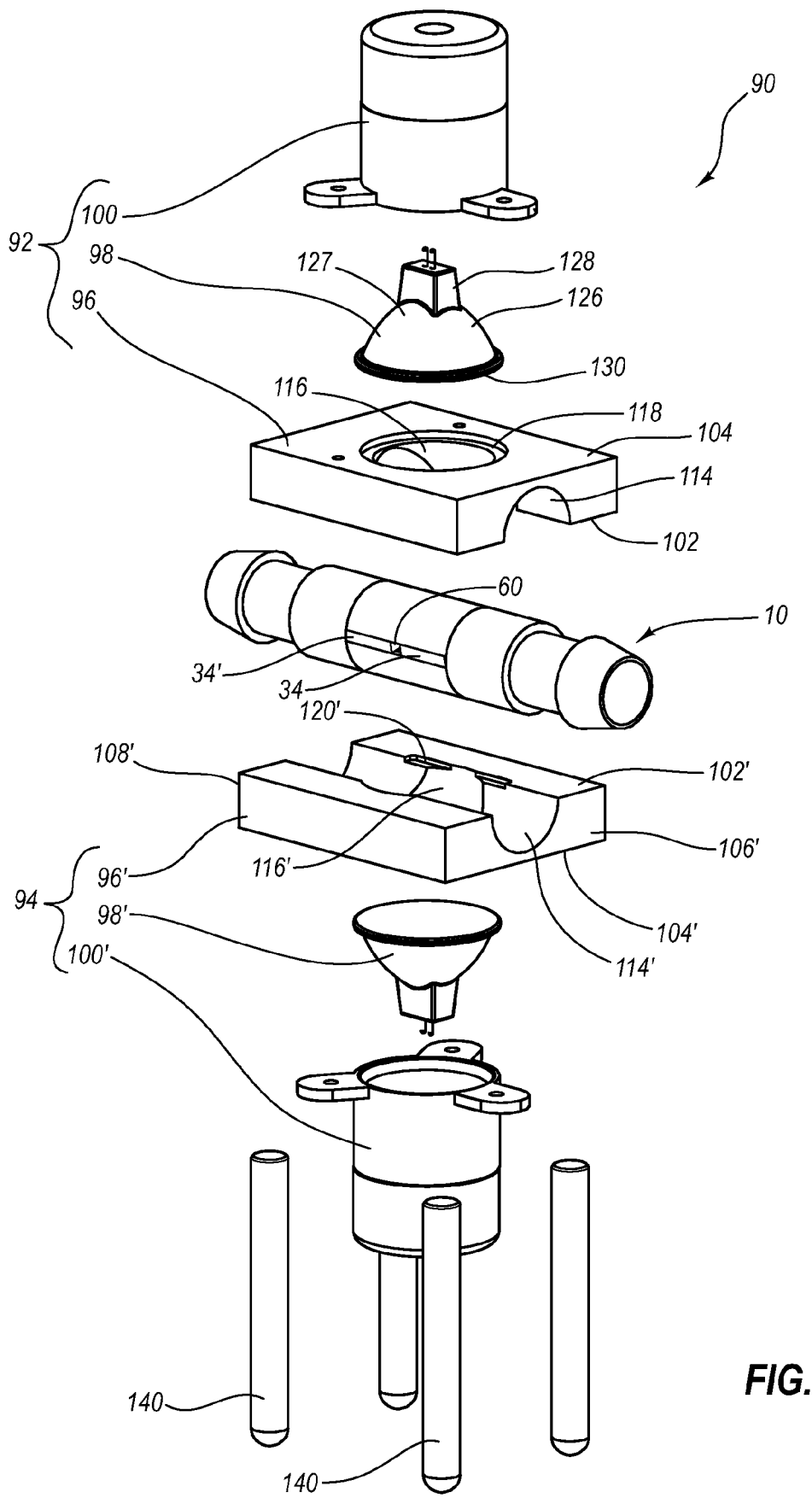
FIG. 9 is an exploded view of the lamp system shown in FIG. 8.

Once membranes 19 and 19' are abutted, radiant energy is applied to the membranes to facilitate their melting as discussed above. Specifically, depicted in FIG. 8 is one embodiment of a lamp system 90 which incorporates features of the present invention and which is configured to apply a radiant energy to connector system 10. As depicted in FIG. 9, lamp system 90 comprises a first lamp assembly 92 and a second lamp assembly 94. It is appreciated that lamp assemblies 92 and 94 have substantially the same configuration. As such, the reference characters, elements, and disclosure with regard to first lamp assembly 92 are also applicable to second lamp assembly 94. To help maintain clarity, an apostrophe "'" is used in association with the reference characters of second lamp assembly 94 where the same reference characters are used to note corresponding elements of first lamp assembly 92.

Figure 10A:
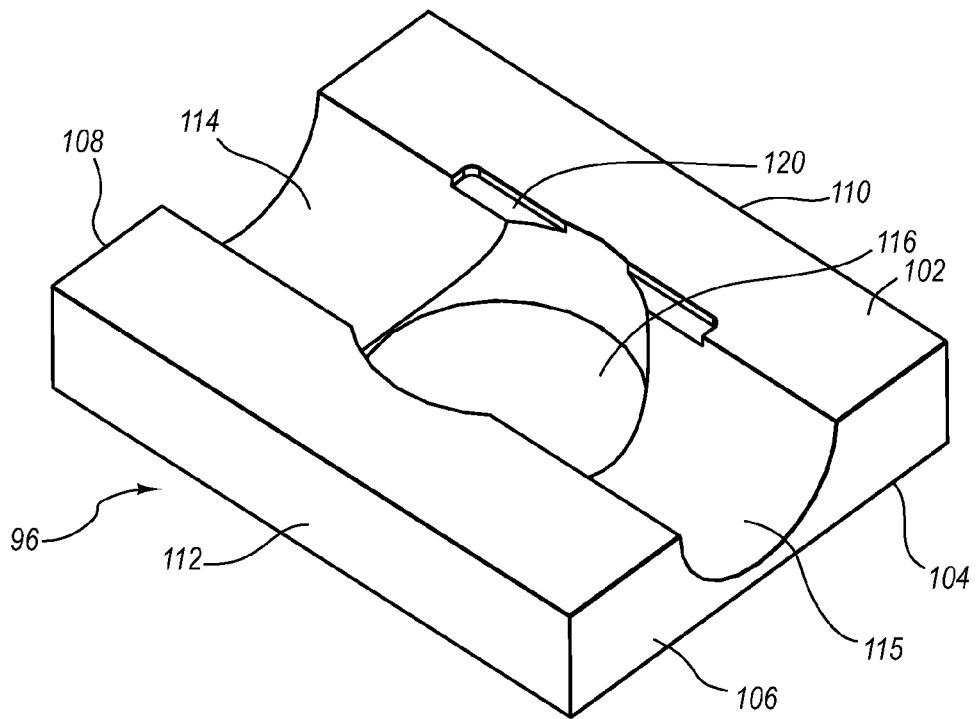
FIG. 10A is a perspective inside view of a saddle shown in FIG. 9.
Figure 10B:
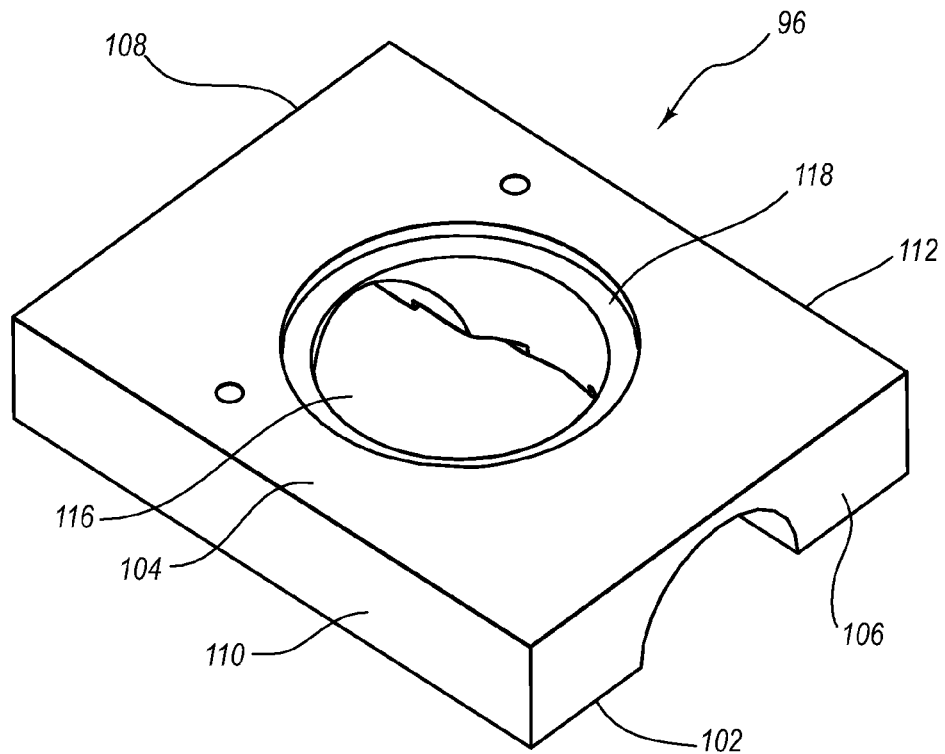
FIG. 10B is a perspective outside view of the saddle shown in FIG. 10A.

In general, first lamp assembly 92 comprises a saddle 96, lamp 98, and a shroud 100. As depicted in FIGS. 10A and 10B, saddle 96 has a generally parallel piped configuration that includes an inside face 102 and an opposing outside face 104 that both extend between opposing end faces 106 and 108 and also between opposing side faces 110 and 112. A substantially semicircular channel 114 is recessed on inside face 102 and centrally extends between opposing end faces 106 and 108. Channel 114 is bounded by a channel surface 115. A circular opening 116 centrally extends from outside face 104 to channel 114. An alignment slot 120 is recessed on inside face 102 at the intersection with channel 114 and opening 116. Alignment slot 120 has substantially the same length as and is configured to receive alignment key 80 as depicted in FIG. 6. An annular recess 118 is formed on outside face 104 and encircles opening 116.

Saddle 96 is typically comprised of a light reflective material such as polished aluminum. Other materials can also be used, especially where a light reflective coating is applied over inside face 102 and channel surface 115. In still other embodiments, saddle 96 can be made of a transparent material or other materials that can provide the desired functional support and withstand the applied radiant energy.

Figure 11:
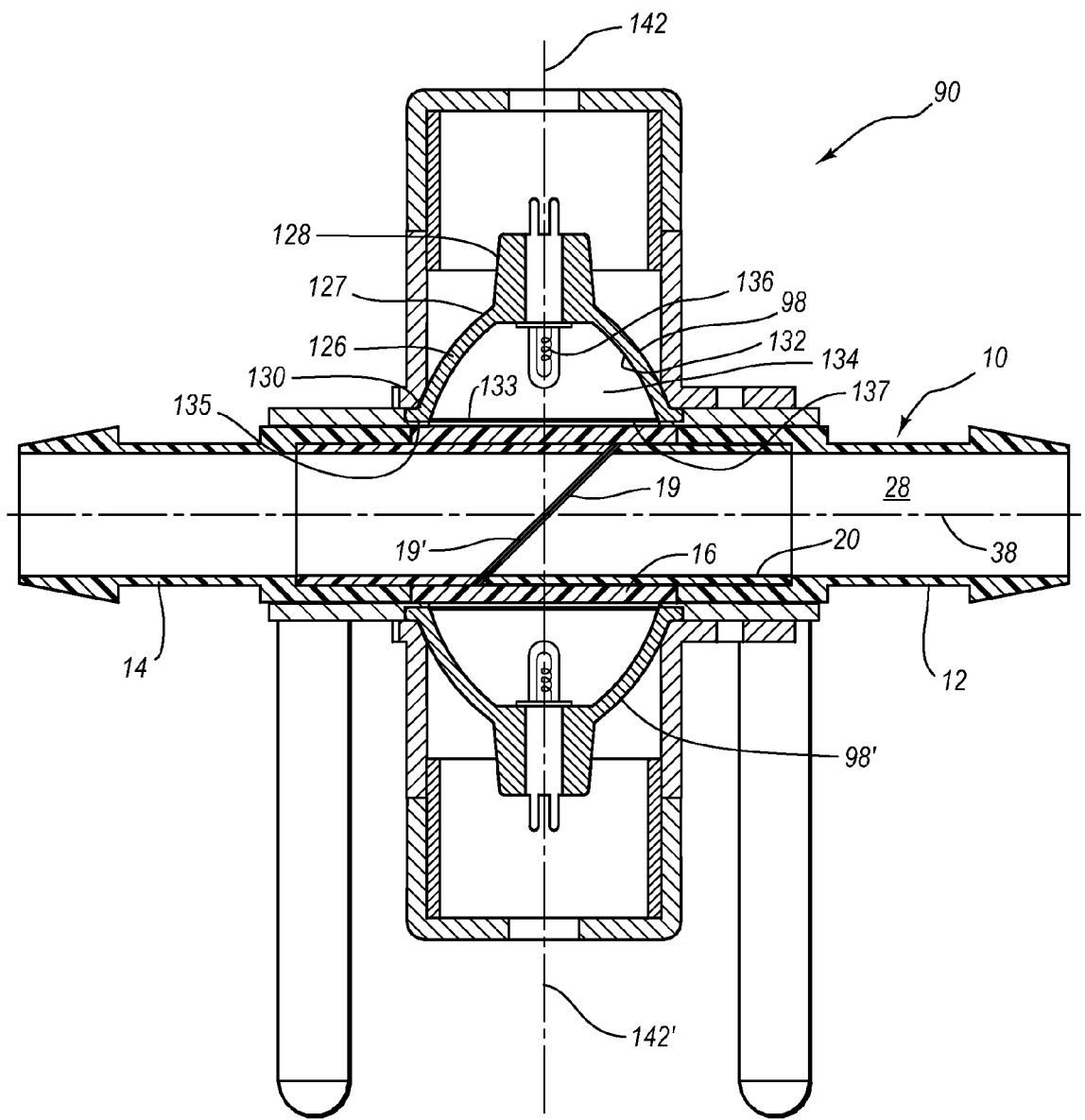
FIG. 11 is a cross sectional side view of the system shown in FIG. 8.

Returning to FIG. 9, in one embodiment of the present invention means are provided for applying a radiant energy to membranes 19 so as to melt membranes 19. By way of example and not by limitation, lamps 98, 98' are one example of such means. In one embodiment lamps 98, 98' comprise incandescent lamps wherein the radiant energy is in the form of a full spectrum light. In general, lamp 98 comprises a cup shaped reflector 126 having a first end 127 at which a plug 128 is formed and an opposing second end 130. Turning to FIG. 11, reflector 126 has an interior surface 132 having a cup shaped contour such as a parabolic configuration. Interior surface 132 partially bounds a compartment 134. An axial filament 136 projects into compartment 134 from first end 127. Light from filament 136 reflects off of interior surface 132 of reflector 126 and is directed out through an opening 137 at second end 130. A transparent window 133 can be used to cover opening 137.

It is appreciated that there are a variety of off the shelf types of incandescent lamps that can be used in the present invention. In general, incandescent lamps vary with respect to size, power, reflector type, and beam shape. Examples of two types of incandescent lamps that can be used in the present invention are spot lamps and projector lamps. Spot lamps emit a divergent beam which produces a more uniform energy disposition. Spot lamps can be purchased that emit light at different spread angles. For example, spot lamps are available with spread angles of 12°, 24°, and 36°. In contrast, projector lamps provide a focus beam which has a higher intensity of light at the center of the beam. The determination of whether a lamp is a spot lamp or a projector lamp is primarily based on the configuration of the reflector for the lamp.

Lamp reflectors can also be classified as a full spectrum reflector or dichroic reflector. Full spectrum reflectors reflect the majority of all radiant energy produced by the filament. That is, such lamps typically reflect about 80% of the light. Such reflectors are typically comprised of polished aluminum or some other metal. In contrast, dichroic reflectors reflect mainly the visible light while the majority of the infrared light is permitted to pass through the reflector. As such, the beam from a dichroic reflector has less radiant energy than from a full spectrum reflector. The inner surface of a reflector can also be comprised of a multimirror reflector surface which produce an average light distribution or a multilens reflector surface which provide a more uniform-like distribution.

Lamps with multimirror reflector surfaces are provided by USHIO America, Inc. under the trademark EUROSTAR while lamps with multilens reflector surfaces are provided by USHIO America, Inc. under the trademark SUPERLINE.

Lamps come in a variety of different sizes measured as the diameter at second end 130. Examples of lamps that can be used in the present invention have a diameter in a range from approximately 2 inches (5 cm) to a diameter of approximately 1 inch (2.5 cm). Lamps can also come in a range of standard powers such as 20 watts, 35 watts, and 50 watts. It is appreciated that other sized and powers can also be used in the present invention.

The lamp selection is in part depended upon the specific application. That is, for small diameter membranes, the lamp selection is less critical because the membranes are more easily melted. To that end, all of the above discussed lamps can be used in melting small diameter membranes. As the membrane increases in size, however, there are increased benefits in selecting the appropriate lamps that will achieve desired melting of the membranes. For efficiency reasons, it is desirable to achieve melting of the membranes 19, 19' in less than 60 seconds and more preferably less than 30 seconds. However, longer periods can also be used. There are several factors that effect melting of membranes 19, 19'. Examples of such factors include the size, thickness, and composition of the membranes; the concentration of pigment within the membranes; and the type and amount of radiant energy applied.

In one specific example for membranes 19, 19' having a maximum diameter greater than 0.5 inches (1.25 cm) and more commonly greater than 0.75 inches (1.9 cm), spot lamps can be used with a 24 degree angle spread having a power rating of 50 watts with a multilens, full spectrum reflector and a 2 inch (5 cm) diameter. Other lamps can also be used. In general, for larger diameter membranes it is desirable to use lamps that uniformly provide a high intensity heat over the entire surface of the membranes.

Returning to FIG. 9, lamp 98 is seated within recess 118 so that the light emitted from lamp 98 shines down through opening 116 of saddle 96. Shroud 100 is placed over top of lamp 98 and is secured to saddle 96. Shroud 100 primarily functions as a holder and a protective cover for lamp 98.

Second lamp assembly 94 has the same configuration and assembly as discussed above with regard to first lamp assembly 92. One distinction, however, is that legs 140 are shown attached to and extending from saddle 96' so as to support lamp system 90.

During use, the assembled connector system 10 is positioned within channel 114' of saddle 96' so that alignment key 80 (FIG. 6) is received within alignment slot 120'. Next, saddle 96 is positioned on top of saddle 96' so that the upper half of connector system 10 is received within channel 114 and the upper half of alignment key 80 is received within alignment slot 120 on saddle 96. If desired, clamps, clips, or other fasteners can be used to hold saddles 96 and 96' together.

In the above loaded configuration, as depicted in FIG. 11, membranes 19, 19' are oriented so as to maximize exposure to lamps 98 and 98' that are disposed on opposing sides thereof. As previously discussed, proper orientation of membranes 19, 19' relative to lamps 98, 98' is ensured by tabs 34, 34' interacting with slot 60 on support member 16 and alignment key 80 interacting with alignment slots 120, 120' (FIGS. 6, 9 and 11). Lamp 98 has a central longitudinal axis 142 that extends between opposing ends 127 and 130. Axis 142 of lamp 98 intersects orthogonally with central axis 38 of connector 12 and is aligned with a corresponding axis 142' of lamp 98'. The intersection of central longitudinal axis 142 with membrane 19' is dependent on the actual orientation of membrane 19' as previously discussed. In the depicted embodiment, the intersection forms an inside angle of approximately 45°. It is also noted that axial filament 136 extends parallel to central axis 142 and thus the same relative orientations can be referenced with regard to central longitudinal axis extending through filament 136. Relative orientations can also be made with reference to a plane in which window 133 of lamp 98 is disposed or with references to a plane in which a distal end face 135 of lamp 98 is disposed.

Once connector system 10 is properly positioned within lamp system 90, lamps 98 and 98' are simultaneously turned on and the light therefrom is passed through saddles 96, 96', support member 16, and housing 17 and 17' so as to shine onto membranes 19 and 19'. As previously discussed, membranes 19 and 19' are designed so that they can initially be heated to a temperature sufficient to destroy all contaminates located on the exterior surfaces of membranes 19 and 19'. Where connector system 10 is not being used for sterile fluids, it is not necessary that membranes 19, 19' be preheated for sterilization.

Figure 12:
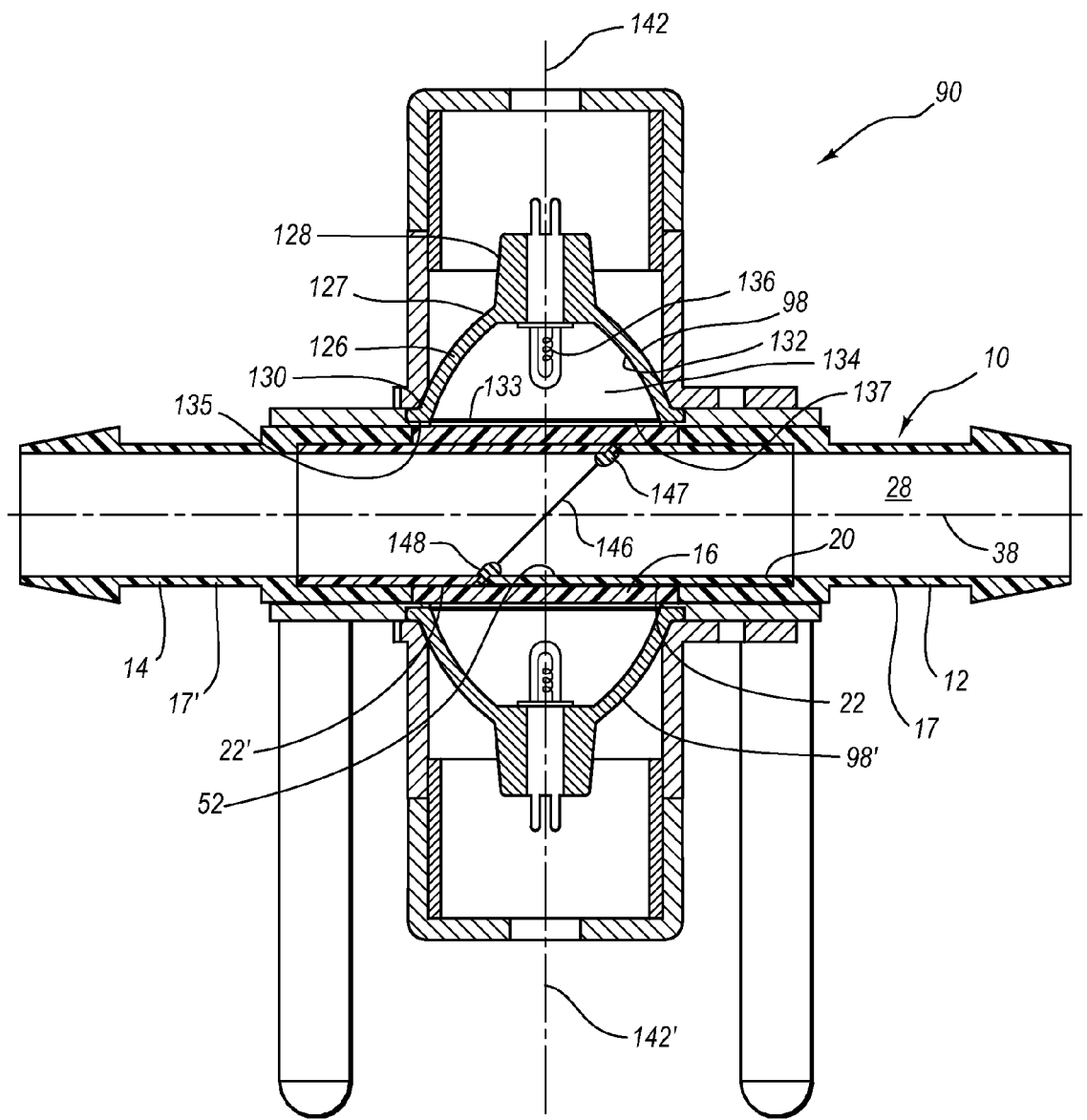
FIG. 12 is a cross sectional side view of the system shown in FIG. 11 wherein the membranes have been melted.

After membranes 19, 19' have been heated at the required temperature and time for sterilization, they are designed to melt. During the melting process, both membranes 19 and 19' begin to melt from the center of the membranes and then melt radially outward toward housings 17, 17'. As a result, a central opening 146 is formed through membranes 19 and 19' as shown in FIG. 12. As members 19, 19' melt, they also melt together which forms a sealed connection between connectors 12 and 14. The melted membranes not only provide a sealed connection between connectors 12 and 14 but also provide a structural connection between connectors 12 and 14. Membranes 19 and 19' that are melted together form an annular sealing ring 147. In some embodiments, a portion of sealing ring 147 does not melt all the way out to interior surfaces 20, 20' of housing 17, 17' so that an annular ridge portion 148 of sealing ring 147 projects a short distance into passage 28.

Once the melting of membranes 19, 19' is completed and the sterile fluid connection in connector system 10 is formed, lamp system 90 is removed. It is noted that support member 16 not only helps facilitate proper alignment of membranes 19, 19' but it also provides increased structural stability to the connection between connectors 12 and 14. That is, support member 16 helps prevent unwanted bending or torsion of first connector 12 relative to second connector 14 which could break the sealed connection between membranes 19 and 19'.

In some embodiments it is desirable to weld or otherwise secure support member 16 to connectors 12 and 14. In part this can be accomplished by a portion of melted membranes 19 and 19' migrating to between exterior surfaces 22, 22' of housings 17, 17' and interior surface 52 of support member 16. As melted membranes 19, 19' cool, a structural bond is formed between housings 17, 17' and support member 16. This connection can be enhanced by having membranes 19, 19' radially extend out partially beyond distal end faces 27, 27' during the initial melting process.

Figure 13A:
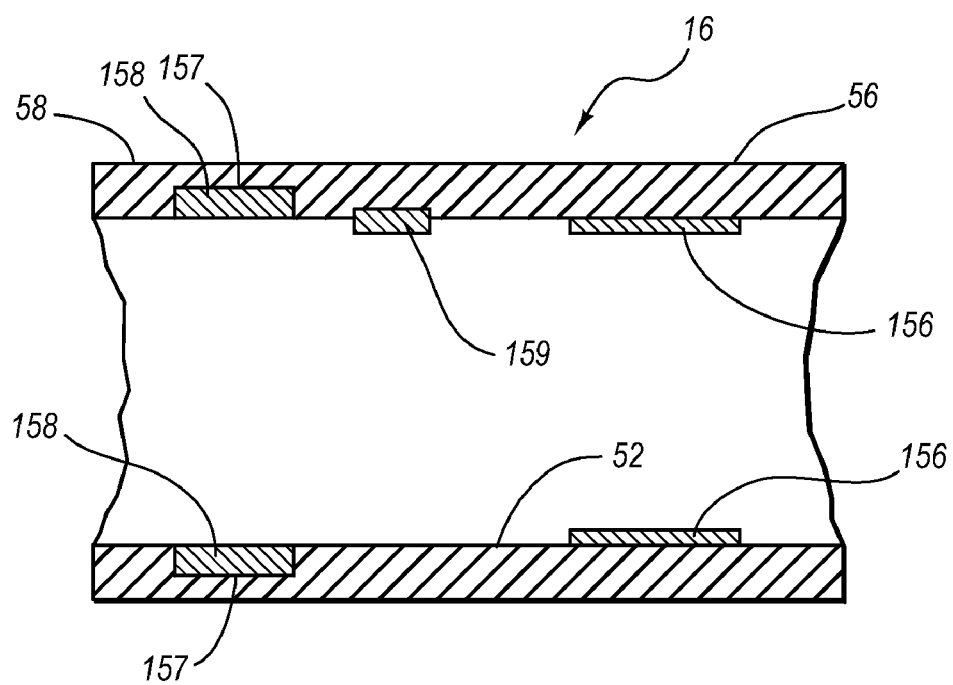
FIG. 13A is a cross sectional side view of an alternative embodiment of the support member shown in FIG. 2.
Figure 13B:
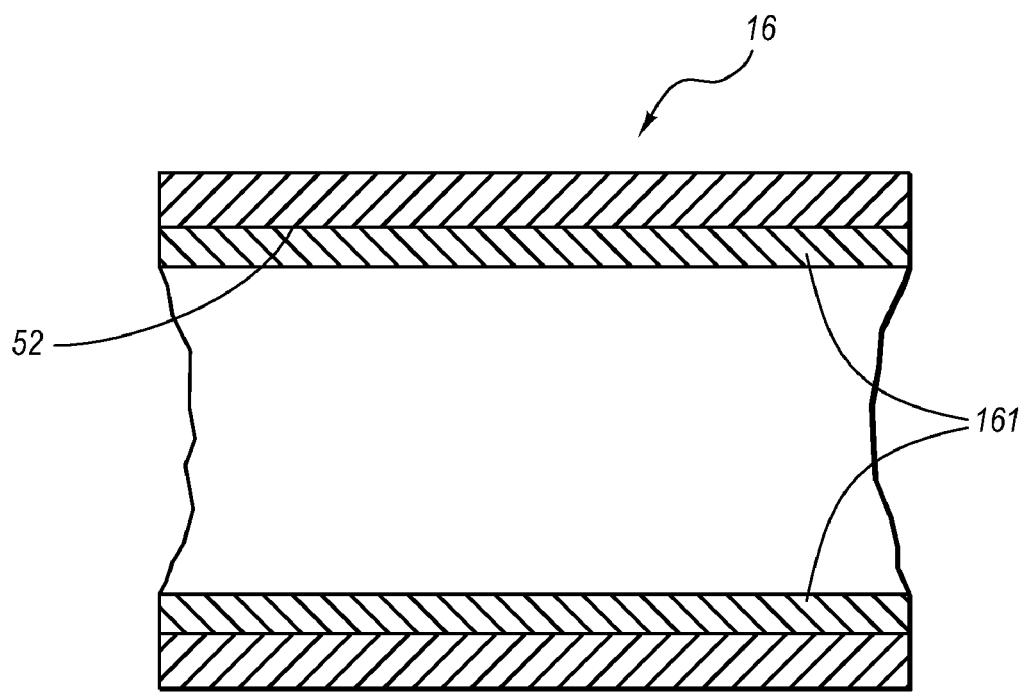
FIG. 13B is a cross sectional side view of an alternative embodiment of a support member having an inner liner.

In yet other embodiments a bonding material can be separately disposed between support member 16 and housings 17 and 17'. For example, as depicted in FIG. 13A, support member 16 is shown having a bonding layer disposed on interior surface 52 thereof. Specifically, in one example, the bonding layer can comprise one or more annular rings 156 that are disposed directly on interior surface 52. In other embodiments one or more annular recesses 157 can be formed on interior surface 52 and the bonding layer can comprise an annular ring 158 disposed within each recess 157. In still other embodiments the bonding layer need not comprise a ring but can comprise one or more discrete patches 159 formed on interior surfaces 52. In yet other embodiments as depicted in FIG. 13B, an annular bonding layer 161 can be disposed so as to completely or at least substantially cover interior surface 52 of support member 16. In contrast or in addition to forming the one or more bonding layers on support member 16, the bonding layers also be formed on exterior surfaces 22, 22' of housings 17, 17' at distal ends 26, 26' (FIG. 1).

The bonding layers can comprise any material that will bond support member 16 and housings 17, 17' together when the radiant energy is applied to melt membranes 19, 19'. In one embodiment the same material used for membranes 19, 19' can also be used for the bonding layers. For example, where support member 16 and housings 17 and 17' are made from an acrylic material, the bonding layers can be comprised of PVDF. However, because the bonding layers will not directly contact the sterile fluid, other materials that would not qualify for membranes 19, 19' can also be used. In contrast to using bonding layers that melt under the applied radiant energy, other welding techniques, adhesives, or fasteners, such as clamps, crimp, or the like, can be used to secure support member 16 around housings 17, 17'.

Figure 14:
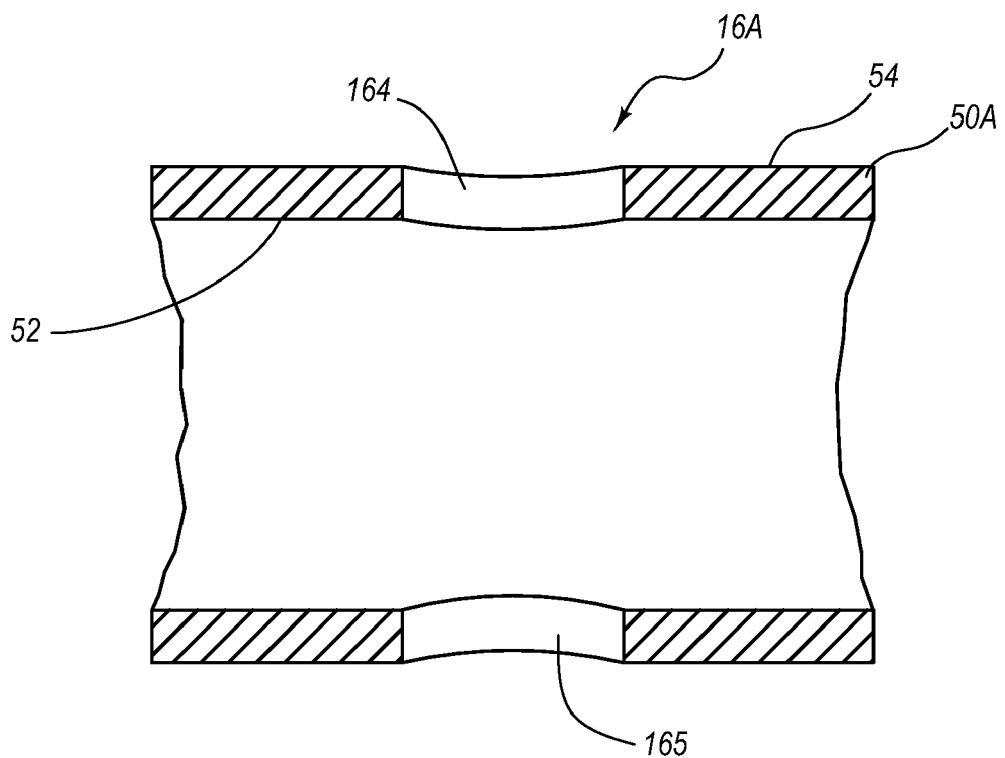
FIG. 14 is a cross sectional side view of another alternative embodiment of a support member having ports extending therethrough.

Depicted in FIG. 14 is an alternative embodiment of a support member 16A. Support member 16A comprises a tubular sleeve 50A that, in contrast to tubular sleeve 50, has a centrally disposed first port 164 and an opposing second port 165 both which extend between exterior surface 54 and interior surface 52. Ports 164 and 165 are configured to align with and have a size comparable to openings 116 and 116' of saddles 96 and 96' (FIG. 9). As a result, the radiant energy from lamps 98 and 98' passes through ports 164 and 165. In this embodiment it is not necessary that support member 16A be comprised of a transparent material. If desired, transparent windows can be disposed within ports 164 and 165. Support member 16A can also be fabricated so that a portion thereof is comprised of a transparent material.

It is appreciated that the support member used to couple together connectors 12 and 14 can come in a variety of different configurations. By way of example and not by limitation, the support member can comprise a two piece member that snaps, screws, bolts, or otherwise connects together around connectors 12 and 14. In another embodiment the support member can comprise a clamp that is hinged so that it can be closed around connectors 12 and 14. In the prior embodiments support member 16 is configured so that it can be separated from connectors 12 and 14. In still other embodiments, the support member can be permanently mounted on one of the connectors for coupling with the other connector. In some embodiments, however, this may be less preferred in that the connectors are then no longer identical and proper matching of the connectors is required for coupling. It is also appreciated that portions of a single support member can be formed on each of connectors 12 and 14. That is, interlocking members such as threaded connections, snap fit connections, bayonet connections, or connections that are made by screws, bolts or other fasteners can be made on connectors 12 and 14 so that they can be connected together without a separate support member.

Figure 15:
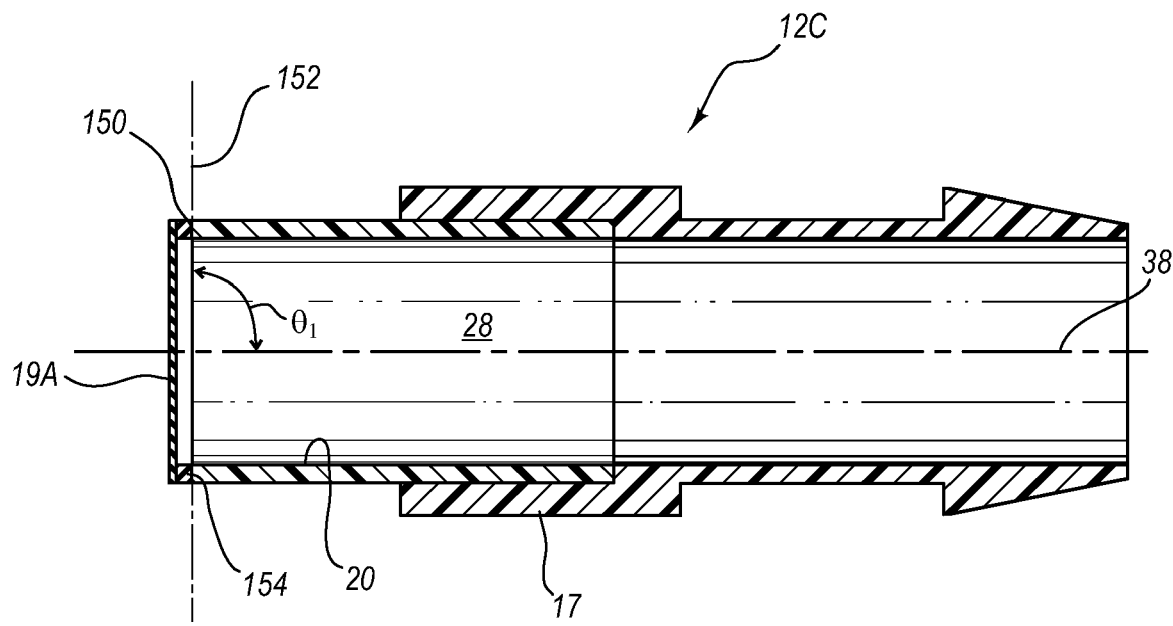
FIG. 15 is a cross sectional side view of an alternative connector wherein the distal end face is perpendicular to the longitudinal axis of the connector.

Depicted in FIG. 15 is another alternative embodiment of a connector 12C incorporating features of the present invention. Like elements between connector 12C and those of the prior connectors are identified by like reference characters. Connector 12C is substantially the same as prior connector 12 or 12B except that connector 12C has a distal end face 150 that is disposed within an imaginary plane 152 that intersects at substantially right angles with central longitudinal axis 38. In other embodiments an inside angle $\theta_1$ formed between imaginary plane 152 and central longitudinal axis 38 can be in a range between about 70° to about 90° or between about 80° to about 90°. Other angles can also be used. A membrane 19A is disposed at the same orientation as imaginary plane 152 relative to longitudinal axis 38. Membrane 19A can be made of the same materials and have the same properties as previously discussed with regard to membrane 19. Although membrane 19A can be connected directly to distal end face 150 using methods previously discussed with regard to membrane 19, in the depicted embodiment an annular ring 154 is disposed between membrane 19A and distal end face 150.

As membrane 19A is heated by the radiant energy, heat dissipates from the perimeter edge of membrane 19A through housing 17. As a result, in some situations membrane 19A may not melt all the way to housing 17. Rather, as previously discussed with regard to FIG. 12, an annular ridge 148 comprised of the melted membranes can radially inwardly project into passageway 28. Annular ridge 148 can restrict flow of fluid through connectors 12 and 14. Furthermore, delicate cells or microorganisms that are being passed through the connectors can strike and be potentially damaged by ridge 148 as they flow thereby.

Accordingly, it can be desirable to have membrane 19A melt all the way to interior surface 20 of housing 17 so as to be substantially flush therewith. By forming ring 154 out of a radiant energy absorbing material, ring 154 is heated during the application of the radiant energy. As a result, ring 154 helps to maintain the heat at the perimeter of membrane 19A which in turn helps the perimeter edge of membrane 19A to melt all the way out to or at least closer to housing 17. In one embodiment ring 154 can comprise the same material as membranes 19, 19A. Other materials as previously discussed with regard to membrane 19 can also be used. In contrast to having a separate ring 154 that is attached between membrane 19A and housing 17, it is also appreciated that membrane 19A could be formed having a thickened perimeter edge so as to achieve the same objective.

It is also appreciated that there are benefits in having membrane 19A disposed perpendicular to central longitudinal axis 38 as opposed to an angle as depicted in FIG. 3. For example, by disposing membrane 19A perpendicular to axis 38, membrane 19A is now circular and smaller than membrane 19 of FIG. 3. From a manufacturing standpoint, it is easier to mount a membrane on a surface that perpendicular to axis 38 than on a surface that is sloped relative to axis 38. Also, as a result of membrane 19A being perpendicular to axis 38 and circular, no alignment is required when abutting membranes 19A and 19A'. As a result, tabs 34 and 34' can be eliminated from connectors 12C and 14C and slot 60 can be eliminated from support member 60 (FIG. 1). Other benefits are also achieved.

Figure 16:
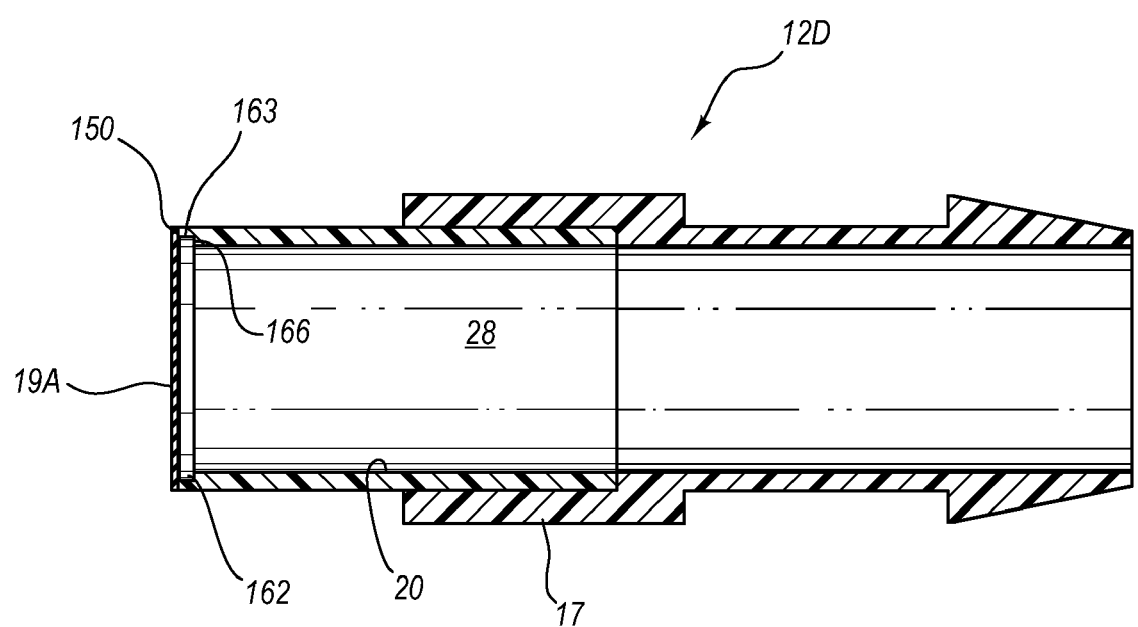
FIG. 16 is a cross sectional side view of an alternative embodiment of the connector shown in FIG. 15 wherein an annular recess is formed adjacent to the membranes.

Depicted in FIG. 16 is another embodiment of a connector 12D incorporating features of the present embodiment. Like elements between connectors 12C and 12D are identified by like reference characters. In contrast to connector 12C, ring 154 has been removed from connector 12D. Furthermore, an annular recess 162 is formed on interior surface 20 adjacent to distal end face 150. Recess 162 is bounded by an annular floor 163 and an annular shoulder 166 that extends between floor 163 and interior surface 20. Recess 162 provides a space for annular ridge 148 (FIG. 12) formed by melted membrane 19A. That is, even if a ridge 148 projects inward away from annular floor 163, ridge 148 would not obstruct the fluid flow and would not create a risk to cells or microorganisms if ridge 148 did not project radially inward from interior surface 20.

Furthermore, even if ridge 148 did project inward from interior surface 20, the use of recess 162 limits flow constriction and the potential for damage to cells or microorganisms.

Figure 17:
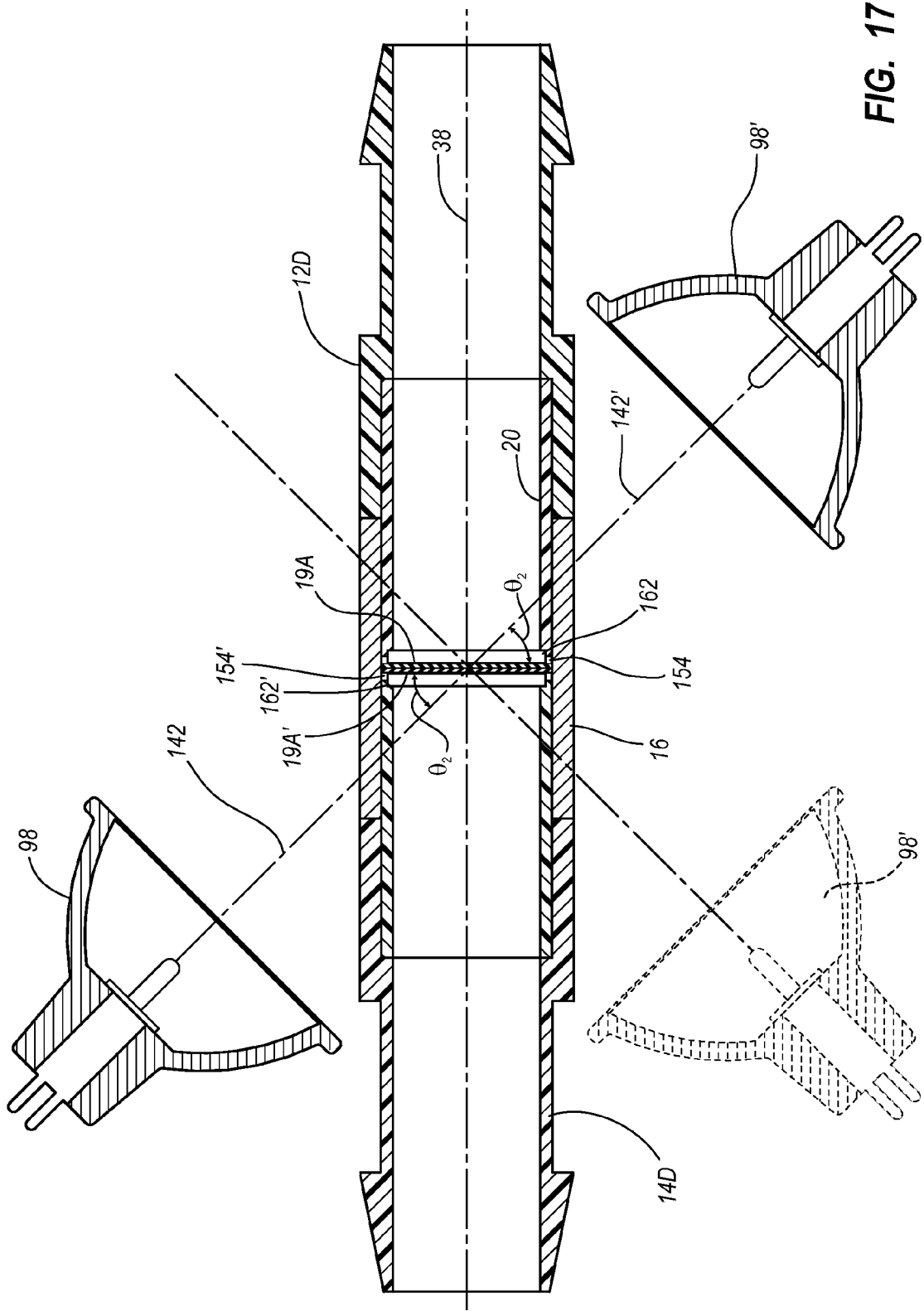
FIG. 17 is a cross sectional side view of a connector system incorporating features from FIGS. 15 and 16 wherein lamps have been rotated to melt the membranes thereof.

Depicted in FIG. 17 is a pair of connectors 12D and 14D. A pair of membranes 19A and 19A' are again disposed substantially perpendicular to central longitudinal axis 38. Furthermore, in this embodiment both of connectors 12D and 14D include recess 162 and ring 154. Once membranes 19A and 19A' are abutted together within support member 16, radiant energy is again used to melt membranes 19A, 19A'. However, because membranes 19A and 19A' are now disposed perpendicular to longitudinal axis 38, lamps 98 and 98' need to be rotated so as to project light onto the face of membranes 19A, 19A'. In one embodiment, lamp 98 is disposed so that central axis 142 of lamp 98 intersects with membrane 19A' at an inside angle $\theta_2$ in a range between about 20θ to about 70° with about 30° to about 60° being common or about 40° to about 50° also being common. Other angles can also be used, particularly where there are changes in the connector and related equipment.

Lamp 98' is also oriented so as to shine on membrane 19A at the same angle $\theta_2$. Thus, in the depicted embodiment lamps 98 and 98' are opposingly facing with their corresponding central axes 142 and 142' being aligned. Although not shown, it is appreciated that saddles 96, 96' and shrouds 100, 100' can be adapted to be used with angled lamps 98 and 98'.

Figure 18:
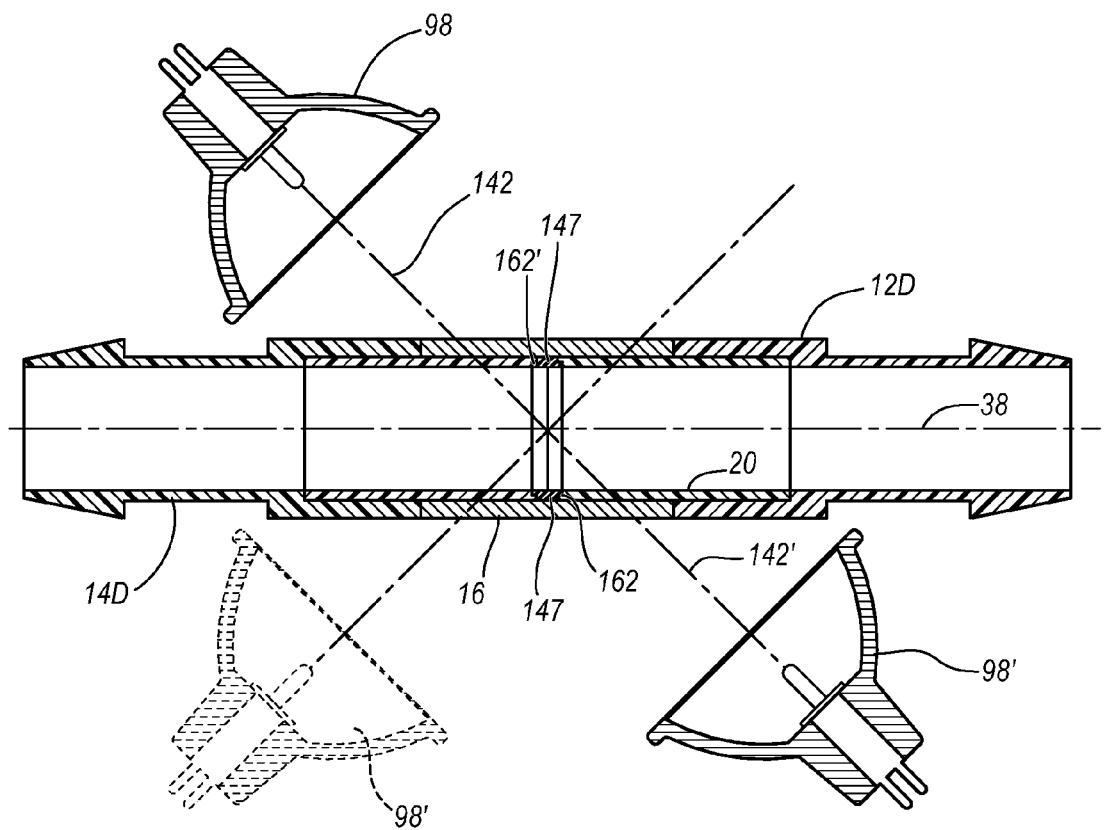
FIG. 18 is a cross sectional side view of the connector system shown in FIG. 17 wherein the membranes have been melted.

In contrast to having lamps 98 and 98' shine on different membranes, it has been discovered that the melting of the membranes also functions if both lamps 98 and 98' are oriented to shine on the same membrane. For example, as shown in dashed lines, lamp 98' can also be oriented to shine on membrane 19A' at the same angle $\theta_2$ as lamp 98 but from the opposite side of connector 14D. Depicted in FIG. 18, membranes 19A and 19A' are shown as being melting into recesses 162, 162' to form sealing ring 147.

Figure 19:
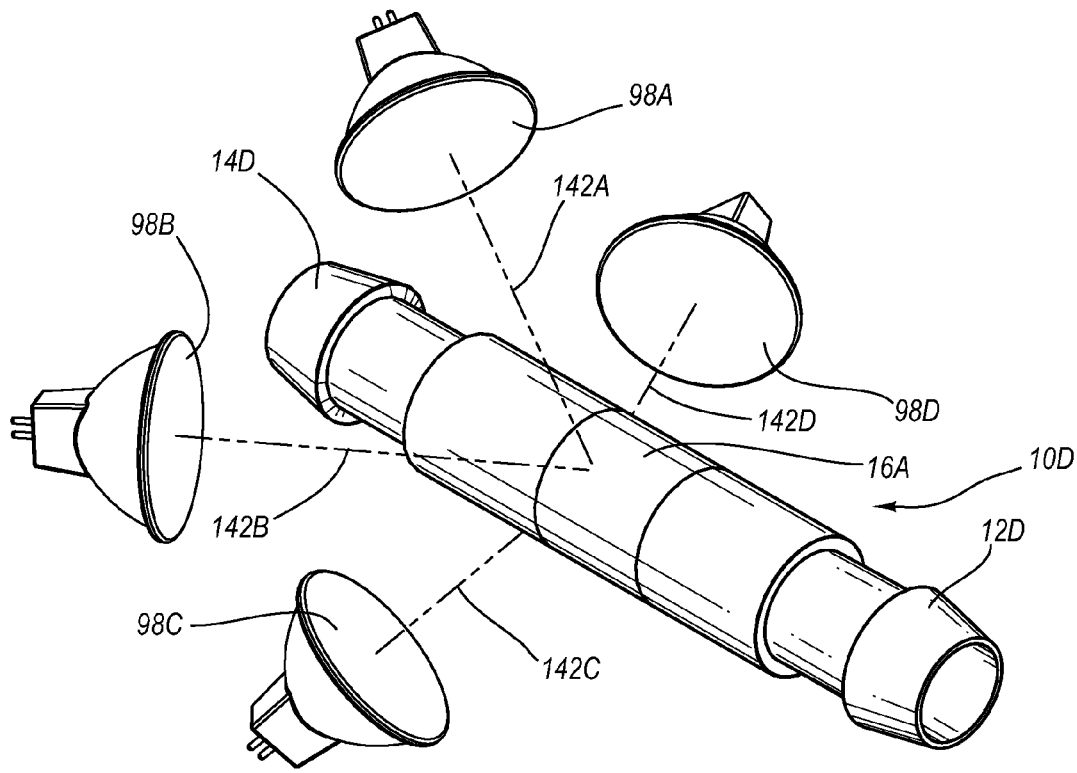
FIG. 19 is a perspective view of the connector system shown in FIG. 18 wherein four lamps are shown for melting the membranes thereof.

To further improve the melting of membranes 19A and 19A' out to or past interior surface 20, it is also appreciated that three or more lamps can be used on one or both of membranes 19A and 19A'. For example, depicted in FIG. 19 is connector system 10D. It noted that because it is no longer necessary to orient membranes 19A and 19A', tabs 34 and 34' have been eliminated from the connectors. Furthermore, slot 60 and key 80 (FIG. 2) have been eliminated to from support member 16A. In this embodiment, four lamps 98A-D are equally radially spaced apart about connector system 10D. Likewise, the central axis 142A-D of each corresponding lamp 98A-D is oriented to be aligned with the center of membrane 19A' (FIG. 17) and to each intersect with membrane 19A' to form the inside angle $\theta_2$ therebetween. In yet other embodiments, two of lamps 98A-D can be directed to shine onto membrane 19A' while the other two are directed to shine onto membrane 19A. Again, a saddle 96 and shroud 100 (FIG. 9) can be adapted to be used with each of lamps 98A-D.

Figure 20:
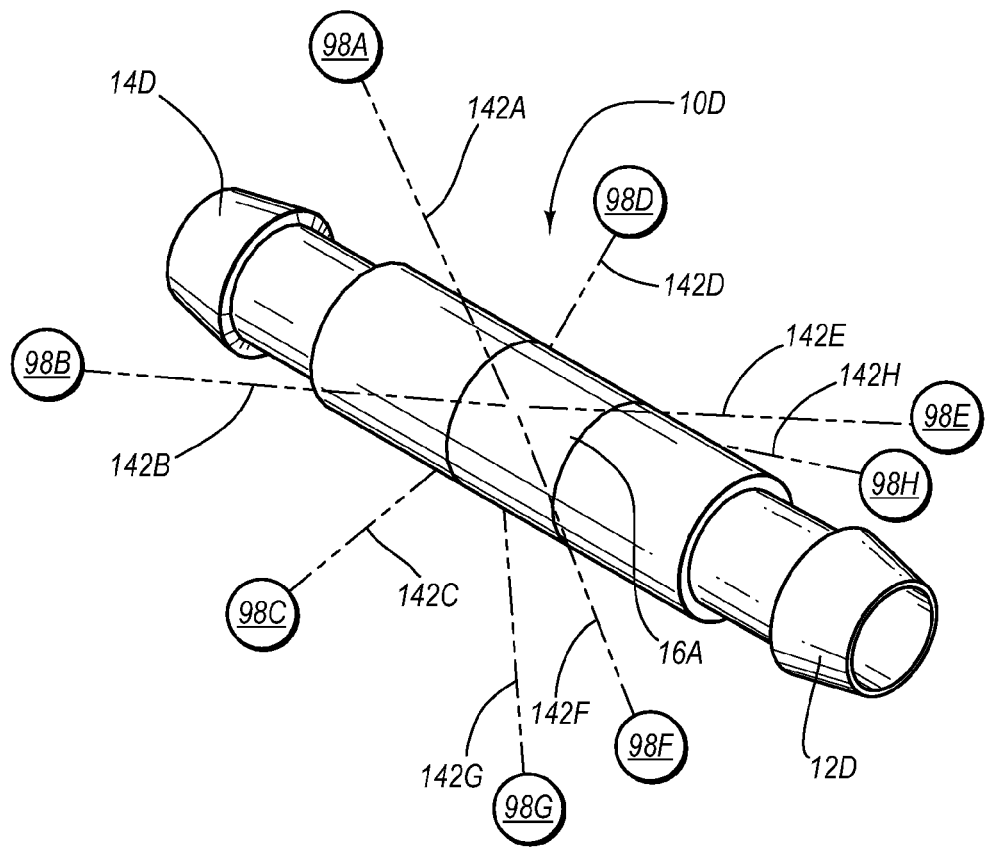
FIG. 20 is a perspective view of the connector system shown in FIG. 19 wherein eight lamps are shown for melting the membranes thereof.

In a further embodiment as depicted in FIG. 20, eight lamps 98A-98H are used. Lamps 98A-D are shown as in FIG. 19 so as to shine on membrane 19A' (FIG. 17) while lamps 98E-H are complementary oriented so as to shine on membrane 19A (FIG. 17). It is appreciated that other numbers of lamps or combinations of different types of lamps can also be used. Furthermore, it is understood that the different numbers and orientations of lamps can also be used in association with connector assembly 10 as depicted in FIG. 7.

Figure 21:
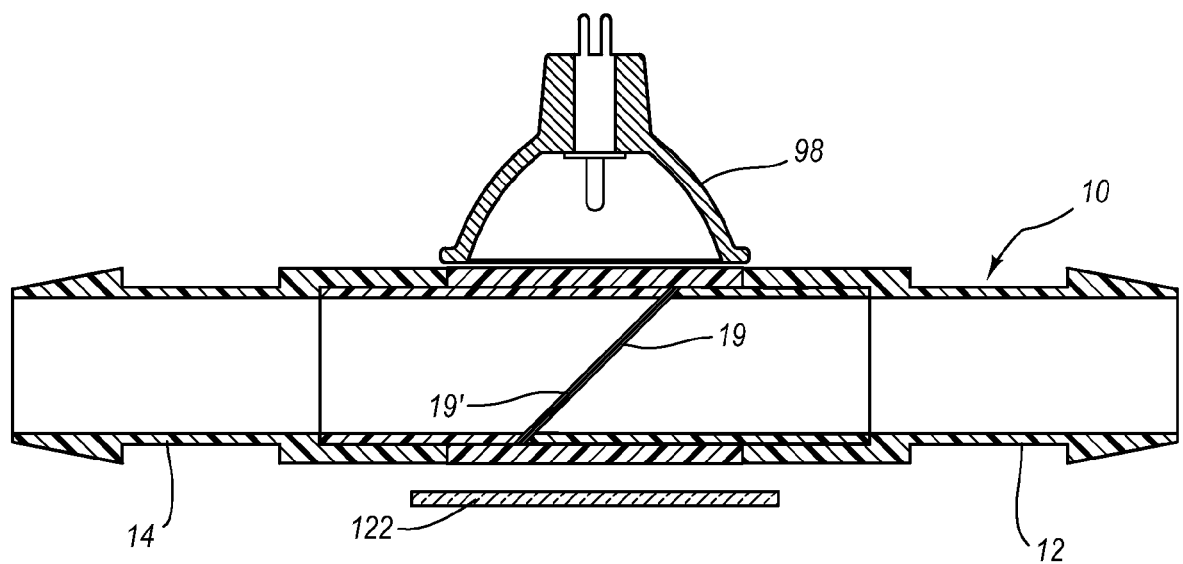
FIG. 21 is a cross sectional side view of an alternative embodiment of a lamp assembly wherein a single lamp is used in association with a mirror.

In contrast to using two or more lamps, it is also appreciated that the radiant energy can be applied to the membranes using a single lamp. For example, in the embodiment depicted in FIG. 21, lamp 98' of FIG. 11 is replaced by a mirror 122. During operation, light that passes down through membranes 19 and 19' from lamp 98 is reflected back up onto the membranes by mirror 122. In this embodiment, improved melting is achieved when membranes 19 and 19' have slightly less pigment so that more radiant energy can pass through membranes 19 and 19' and be reflected by mirror 122. However, sufficient pigment must still be added to enable heating and melting of membranes 19 and 19'.

In the foregoing examples, the means for emitting radiant energy onto the membranes is disclosed as comprising incandescent lamps. It is appreciated, however, that other sources can also be used for emitting radiant energy onto the membranes. In general, the radiant energy can be of any type that can shine or transmit through support member 16 and housings 17 so as to strike and melt the membranes without deteriorating housings 17 or support member 16. By way of example and not by limitation, other sources of radiant energy that can be used in the present invention include infrared lamps, lasers, laser diodes, light emitting diodes, and sources that produce electro magnetic energy that correspond to the energy absorbent pigment. That is, the type of pigment used can vary based on the type or source for the radiant energy.

Figure 22:
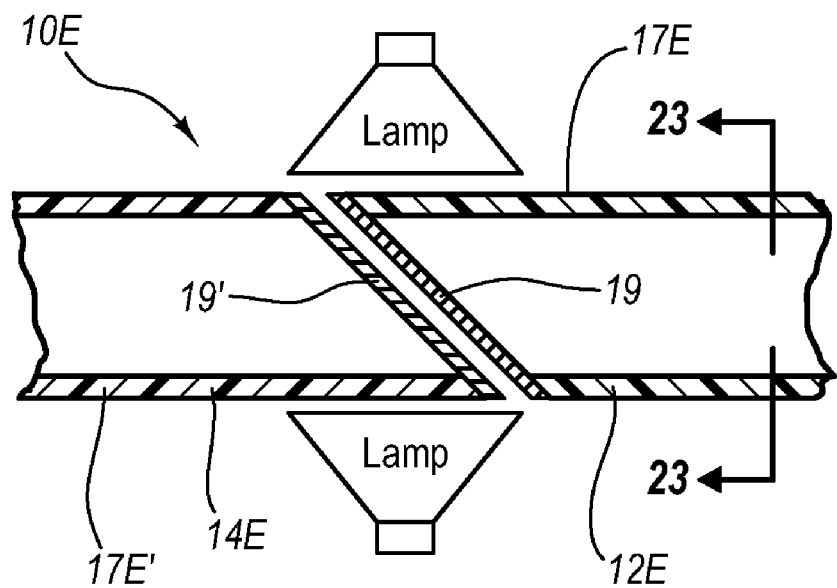
FIG. 22 is a cross sectional side view of an alternative embodiment of a connector system having an exterior surface with flat sides.
Figure 23:
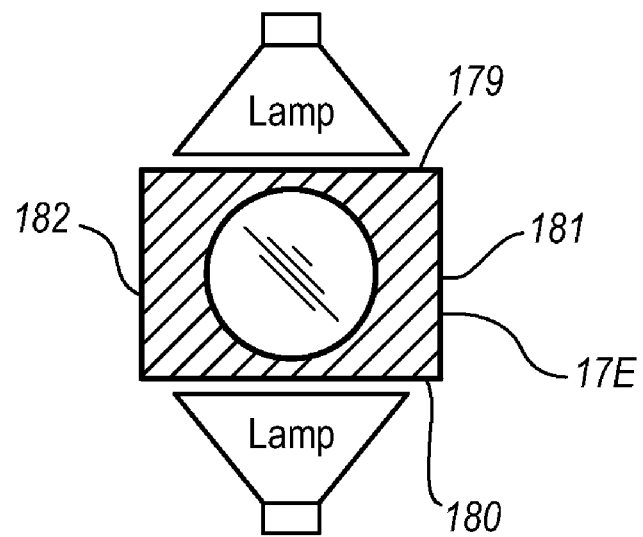
FIG. 23 is a cross sectional end view of the connector system shown in FIG. 22 taken along lines 23-23.

In the prior embodiments, housing 17 and support member 16 are shown having a substantially circular exterior surface. As a result, saddles 96 and 96' with channels 114 and 114' (FIG. 9) are used to provide a stable support surface for lamps 98 and 98'. In one alternative embodiment as depicted in FIGS. 22 and 23, a connector system 10E is shown. Connector system 10E comprises a first connector 12E comprising a tubular housing 17E having membrane 19 mounted on a distal end face thereof. A second connector 14E is also shown comprising a housing 17E' having membrane 19' mounted on a distal end face thereof.

In contrast to having a circular exterior surface as previously discussed with regard to connector system 10, each housing 17E and 17E' has a substantially square transverse cross section. That is, as depicted in FIG. 23, each housing 17E and 17E' has a substantially flat top surface 179 and a flat bottom surface 180 each extending between opposing flat side surfaces 181 and 182. In this configuration, each surface 179-182 forms a flat support surface on which a lamp can be directly mounted. In one alternative, side surfaces 181 and 182 need not be flat where lamps are not mounted thereon. Likewise, not all of top surface 179 and bottom surface 180 need to be flat but only a portion thereof sufficient to receive the lamps. If desired, a support member having an interior surface complimentary to housings 17E and 17E' and having an exterior surface with corresponding flat surfaces can also be used. It is appreciated that shoulder 32 and barb 30 (FIG. 2) and the alternatives previously discussed therewith can be used with housings 17E and 17E'.

Figure 24:
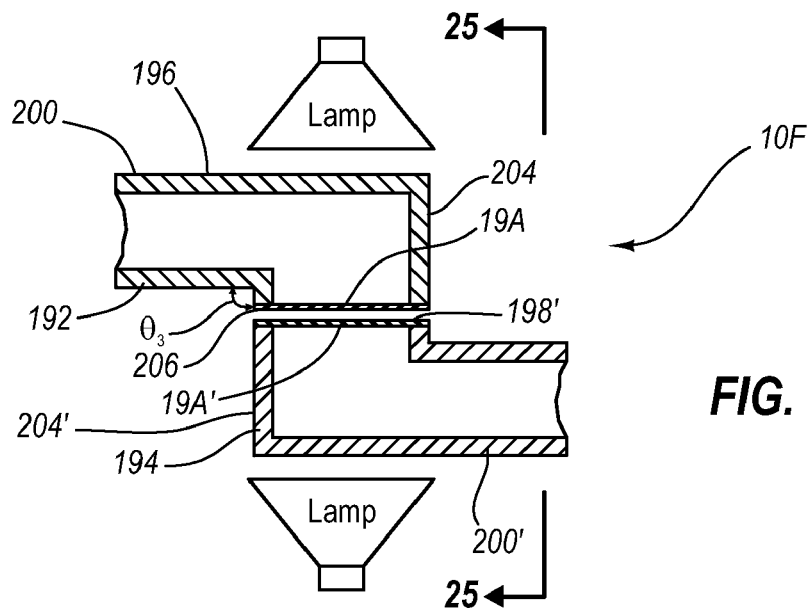
FIG. 24 is a cross sectional side view of an alternative embodiment of a connector system having an angled flow path.
Figure 25:
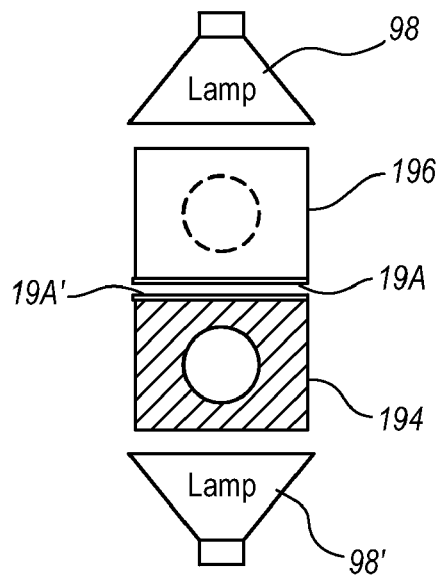
FIG. 25 is a cross sectional side view of a connector system shown in FIG. 24 taken long section line 25-25.
Figure 26:
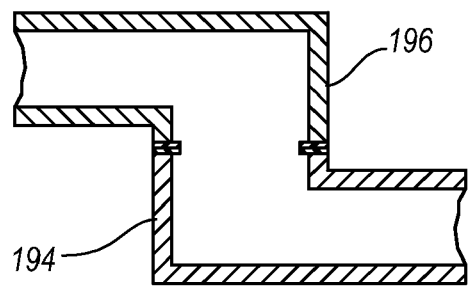
FIG. 26 is a cross section side view of the connector system shown in FIG. 24 wherein the membranes have been melted.

In the prior embodiments each connector system is designed so as to have a linear flow path extending therethrough. This linear flow path eliminates turns or corners that can potentially damage delicate cells or microorganisms. In alternative embodiments, however, it is also appreciated that connectors can be formed which form an angled flow path extending therethrough. For example, depicted in FIGS. 24-26 is a connector system 10F incorporating features of the present invention. Connector system 10F comprises a first connector 192 and a second connector 194 each having the same configuration. First connector 192 comprises a tubular housing 196 having a membrane 19A mounted on an end thereof. Housing 196 comprises a tubular first stem 200 and a tubular second stem 204. Second stem 204 is fluid coupled with and orthogonally projects from first stem 200. Second stem 204 has a distal end face 206 on which membrane 19A is disposed. Second connector 194 has a configuration complementary to first connector 192 so that membranes 19A and 19A' can be biased against each other.

As with connector system 10E, the exterior surface of connectors 192 and 194 are each comprised of a plurality of flat faces on which lamps 98 and 98' can be mounted. It is appreciated that some faces need not be flat and/or that only a portion of some faces may be flat. In one alternative, second stem 204 need not project orthogonally from first stem 200 but can project so as to form an angle $\theta_3$ in a range between about 45° to about 135° with about 75° to about 105° being more common. Other angles can also be used.

The present invention may be embodied in other specific forms without departing from its spirit or essential characteristics. For example, it is appreciated that the different components and features of each of the different connector systems can be mixed and matched to provide other alternative configurations. Thus the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A connector comprising:
    a tubular body having a proximal end terminating at a proximal end face and an opposing distal end terminating at a distal end face, the tubular body having an interior surface bounding a linear passage extending therethrough between the proximal end face and the opposing distal end face, the passage having a central longitudinal axis extending along the length thereof, the linear passage having a cross sectional area normal to the central longitudinal axis that is substantially constant along the length of the linear passage, an annular barb encircling and radially outwardly projecting from the proximal end of the tubular body; and
    a membrane secured to the distal end face of the tubular body so as to seal the passage closed thereat without encircling the tubular body, the membrane being disposed in a plane that orthogonally intersects with the central longitudinal axis of the tubular body, the membrane and the body being configured so that when a radiant energy is applied to the membrane and the body, at least a portion of the membrane exposed to the radiant energy melts to form an opening therein and at least a portion of the body exposed to the radiant energy does not melt.

2. The connector as recited in claim 1, wherein the membrane is mounted directly on the distal end face of the tubular body.

3. The connector as recited in claim 1, further comprising an annular ring having a first side connected to the distal end face of the tubular body and an opposing second side connected to the membrane.

4. The connector as recited in claim 1, further comprising a shoulder radially outwardly projecting from the body at a location between the proximal end face and the distal end face.

5. The connector as recited in claim 1, wherein the membrane has a maximum diameter in a range between about 2 cm and about 5 cm.

6. The connector as recited in claim 1, wherein the membrane is comprised of a thermoplastic.

7. The connector as recited in claim 1, wherein the membrane is comprised of polyvinylidene fluoride.

8. The connector as recited in claim 1, wherein the tubular body comprises:
    a tubular liner comprised of a first polymeric material that bounds the linear passage; and
    an outer layer comprised of a second polymeric material that encircles the tubular liner, the second polymeric material being different than the first polymeric material.

9. The connector as recited in claim 1, wherein the body has an exterior surface extending between the proximal end face and the distal end face, the membrane terminating at an outside edge of the distal end face so that the membrane does not extend over a portion of the exterior surface of the body.

10. The connector as recited in claim 1, wherein the entire membrane comprises a flat, planar sheet.

11. A system for forming a fluid connection, the system comprising:
    a first connector comprising:
        a tubular first body having a linear first passage extending therethrough between a proximal end and an opposing distal end, the first passage having a central first longitudinal axis extending along the length thereof; and
        a first membrane sealing the first passage closed at the distal end of the first body without encircling the first body, the central first longitudinal axis intersecting with the first membrane so as to form an angle therebetween in a range between about 20° and about 70°;
    a second connector comprising:
        a tubular second body having a linear second passage extending therethrough between a proximal end and an opposing distal end, the second passage having a central second longitudinal axis extending along the length thereof; and
        a second membrane sealing the second passage closed at the distal end of the second body, the first membrane and the second membrane being adapted to melt under the application of radiant energy; and
    the distal end of the first body being coupled to the distal end of the second body so that the first longitudinal axis is aligned with the second longitudinal axis and the first membrane is disposed against or adjacent to the second membrane.

12. The system for forming a fluid connection as recited in claim 11, further comprising a support member coupling the distal end of the first body to the distal end of the second body, the support member being separable from the first connector and the second connector.

13. The system for forming a fluid connection as recited in claim 12, wherein the support member comprises a tubular sleeve, at least a portion of the distal end of the first body and the distal end of the second body being received within the tubular sleeve.

14. The system for forming a fluid connection as recited in claim 11, wherein the membrane is comprised of a fluoropolymer.

15. The system for forming a fluid connection as recited in claim 11, wherein the membrane is comprised of polyvinylidene fluoride.

16. The system for forming a fluid connection as recited in claim 11, wherein the first connector and the second connector have substantially the same configuration.

17. A system for forming a fluid connection, the system comprising:
    a first connector comprising:
        a tubular first body having a first passage extending therethrough between a proximal end and an opposing distal end, the first passage having a first longitudinal axis extending along the length thereof; and a first membrane sealing the first passage closed at the distal end of the first body without encircling the first body, the first longitudinal axis intersecting with the first membrane so as to form an angle therebetween in a range between about 20° and about 70°;

a second connector comprising:
  a tubular second body having a second passage extending therethrough between a proximal end and an opposing distal end, the second passage having a second longitudinal axis extending along the length thereof; and
  a second membrane sealing the second passage closed at the distal end of the second body, the first membrane and the second membrane being adapted to melt under the application of radiant energy; and a support member coupling the distal end of the first body to the distal end of the second body, the support member being separable from the first connector and the second connector.

18. The system for forming a fluid connection as recited in claim 17, wherein the support member comprises a tubular sleeve, at least a portion of the distal end of the first body and the distal end of the second body being received within the tubular sleeve.

19. The system for forming a fluid connection as recited in claim 17, further comprising a slot formed on the support member, a tab projecting from the first body being received within the slot of the support member.

20. The system for forming a fluid connection as recited in claim 17, wherein the support member comprises a tubular sleeve having a substantially C-shaped transverse cross section with an elongated slot that extends between a first end and an opposing second end, at least a portion of the distal end of the first body and the distal end of the second body being received within the tubular sleeve.

21. The system for forming a fluid connection as recited in claim 17, wherein the support member is comprised of a transparent material.

22. The system for forming a fluid connection as recited in claim 17, wherein the membrane is comprised of a fluoropolymer.

23. The system for forming a fluid connection as recited in claim 17, wherein the membrane is comprised of polyvinylidene fluoride.

24. A connector comprising:
  a tubular body having a proximal end terminating at a proximal end face and an opposing distal end terminating at a distal end face, the tubular body having an interior surface bounding a linear passage extending therethrough between the proximal end face and the opposing distal end face, the passage having a central longitudinal axis extending along the length thereof, the tubular body comprising:
    a tubular liner comprised of a first polymeric material that bounds the linear passage; and
    an outer layer comprised of a second polymeric material that encircles the tubular liner, the second polymeric material being different than the first polymeric material; and
  a membrane secured to the distal end of the tubular body so as to seal the passage closed thereat, the membrane being disposed in a plane that orthogonally intersects with the central longitudinal axis of the tubular body, the membrane and the body being configured so that when a radiant energy is applied to the membrane and the body, at least a portion of the membrane exposed to the radiant energy melts to form an opening therein and at least a portion of the body exposed to the radiant energy does not melt.

25. A system for forming a fluid connection, the system comprising:
  a first connector comprising:
    a tubular first body having a first passage extending therethrough between a proximal end and an opposing distal end, the first passage having a first longitudinal axis extending along the length thereof; and
    a first membrane sealing the first passage closed at the distal end of the first body;
  a second connector comprising:
    a tubular second body having a second passage extending therethrough between a proximal end and an opposing distal end, the second passage having a second longitudinal axis extending along the length thereof; and
    a second membrane sealing the second passage closed at the distal end of the second body, the first membrane and the second membrane being adapted to melt under the application of radiant energy; and
  a support member coupling the distal end of the first body to the distal end of the second body, a slot formed on the support member, a tab projecting from the first body being received within the slot of the support member, the support member being separable from the first connector and the second connector.

26. A system for forming a fluid connection, the system comprising:
  a first connector comprising:
    a tubular first body having a first passage extending therethrough between a proximal end and an opposing distal end, the first passage having a first longitudinal axis extending along the length thereof; and
    a first membrane sealing the first passage closed at the distal end of the first body;
  a second connector comprising:
    a tubular second body having a second passage extending therethrough between a proximal end and an opposing distal end, the second passage having a second longitudinal axis extending along the length thereof; and
    a second membrane sealing the second passage closed at the distal end of the second body, the first membrane and the second membrane being adapted to melt under the application of radiant energy; and
  a support member coupling the distal end of the first body to the distal end of the second body, the support member comprising a tubular sleeve having a substantially C-shaped transverse cross section with an elongated slot that extends between a first end and an opposing second end, at least a portion of the distal end of the first body and the distal end of the second body being received within the tubular sleeve, the support member being separable from the first connector and the second connector.

* * * * *

UNITED STATES PATENT AND TRADEMARK OFFICE
CERTIFICATE OF CORRECTION

PATENT NO. : 7,938,454 B2
APPLICATION NO. : 11/739433
DATED : May 10, 2011
INVENTOR(S) : Buchanan et al.

Page 1 of 2

It is certified that error appears in the above-identified patent and that said Letters Patent is hereby corrected as shown below:

Drawings
Sheet 17, replace Figure 24 with the figure depicted below, wherein label 198' is changed to 206'

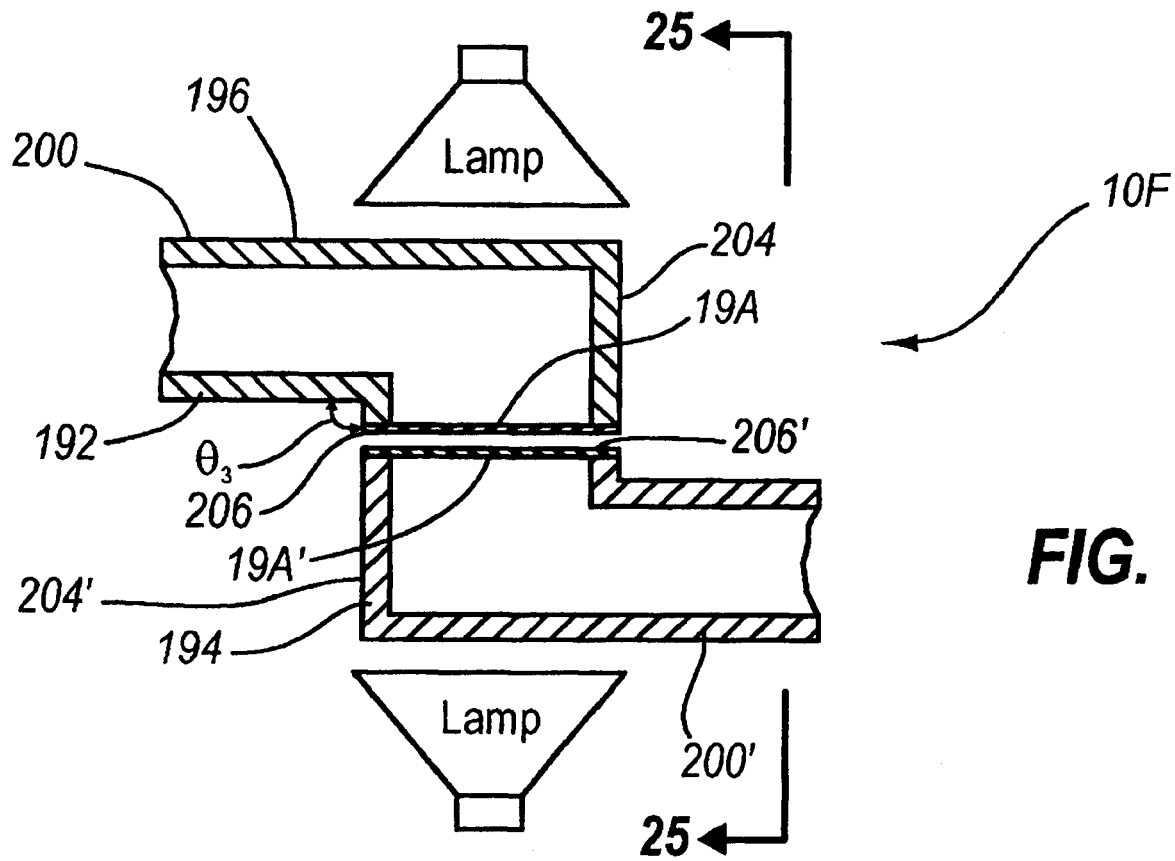

Signed and Sealed this
Eighth Day of November, 2011

David J. Kappos
*Director of the United States Patent and Trademark Office*

Column 6
Line 47, change "shoulder 72" to --shoulder 32--

Column 7
Line 8, change "sleeve 32" to --shoulder 32--
Line 16, change "sleeve 32" to --shoulder 32--

Column 10
Line 67, change "provide" to --provides--

Column 14
Line 47, change "that perpendicular" to --that is perpendicular--
Line 53, change "60" to --16--

Column 15
Line 16, change "20θ" to --20°--
Line 43, change "eliminated to from" to --eliminated from--